(12) United States Patent
Fürstner et al.

(10) Patent No.: US 7,026,478 B2
(45) Date of Patent: Apr. 11, 2006

(54) IRON CATALYZED CROSS COUPLING REACTIONS OF AROMATIC COMPOUNDS

(75) Inventors: Alois Fürstner, Mülheim an der Ruhr (DE); Andreas Leitner, Mülheim an der Ruhr (DE); María Méndez, Mülheim an der Ruhr (DE)

(73) Assignee: Studiengesellschaft Kohle mbH, Mulheim an der Ruhr (DE)

( * ) Notice: Subject to any disclaimer, the term of this patent is extended or adjusted under 35 U.S.C. 154(b) by 62 days.

(21) Appl. No.: 10/143,404

(22) Filed: May 10, 2002

(65) Prior Publication Data

US 2003/0220498 A1 Nov. 27, 2003

(51) Int. Cl.
*C07D 237/00* (2006.01)
*C07D 237/02* (2006.01)
*C07D 487/00* (2006.01)
*C07D 251/00* (2006.01)
*C07D 239/02* (2006.01)
*C07D 215/00* (2006.01)
*C07D 215/04* (2006.01)
*C07D 215/12* (2006.01)
*C07C 69/76* (2006.01)
*C07C 303/00* (2006.01)

(52) U.S. Cl. ............... 544/216; 544/224; 544/264; 544/315; 544/353; 544/410; 546/152; 546/173; 546/139; 546/349; 546/350; 549/86; 549/460; 558/56; 558/357; 548/152; 560/103; 564/90; 585/454

(58) Field of Classification Search ............... 544/216, 544/224, 264, 315, 336, 353, 410; 546/152; 546/173, 349, 350, 139; 548/152; 549/86, 549/460; 560/8, 103; 558/56, 357; 564/90; 570/144; 585/454

See application file for complete search history.

(56) References Cited

U.S. PATENT DOCUMENTS 5,211,889 A * 5/1993 Rieke .................. 260/665 R

OTHER PUBLICATIONS

Bezmenova and Kamakin, "Reaction of Sulfolane and its derivatives with a Grignard Reagent" Khimiya Seraorganicheskikh Soedinenii, Soderzhashchkhsya v Neftyakh i Nefteproduktakh, vol. 8, pp. 140-144 (1968) CAPLUS Abstract.*
Oda and Yamamoto, "Reaction of Dimethyl Sulfoxide with Grignard Reagents" J. Org. Chem. vol. 26, pp. 4679-4681 (1961).*
Loader and Anderson, "Pyrrole Chemistry, Part XI. Some Reactions of the Pyrrole Grignard Reagent with Alkyl Carbonates and Alkyl Thiocarbonates" Canadian Journal of Chemistry, vol. 49, pp. 45-48 (1971).*
Quintin et al, "Iron-Catalysed arylation of heteroaryl halides by Grignard reagents" Tetrahedron Letters, vol. 43, pp. 3547-3549 (May 6, 2002).*
Furstner et al, "Iron-Catalyzed Cross-Coupling Reactions" J. Am. Chem. Soc. vol. 124, pp. 13856-13863 (2002).*
Minato et al, "Palladium-Phosphine Complex Catalyzed Cross-Coupling Reaction of 1-Methyl-2-Pyrrolyl-Magnesium Bromide and -Zinc Chloride with Organic Halides" Tetrahedron Letters, vol. 22(52), pp. 5319-5322 (1981).*
Bumagin et al, "Reactions of organometallic compounds catalyzed by transition-metal complexes. Palladium-catalyzed cross-coupling of vinylmagnesium bromide with aryl iodides" Metalloorganicheskaya Khimiya vol. 2(3), pp. 605-610 (1989). CAS Online ABST.*
Weichert et al, "Palladium(0) Catalyzed Cross Coupling Reactions of Hindered, Double activated Aryl Halides with Organozinc Reagents—The Effect of Copper(I) Cocatalysts" Synlett, vol. 5, pp. 473-474 (1996).*
Miller and Farrell, "Synthesis of Functionally Substituted Unsymmetrical biaryls via a Novel Double Metal Catalyzed Coupling Reaction" Tetrahedron Letters, vol. 39, pp. 7275-7278 (1998).*
Wu et al, "Organocalcium Chemistry: Preparation and Reactions of Highly Reactive Calcium" J. Org. Chem., vol. 55, pp. 5045-5051 (1990).*
Cahiez and Avedissian, "Highly Stereo and Chemoselective iron-Catalyzed Alkenylation of Organomagnesium Compounds" SYTHESIS, vol. 8, pp. 1199-1205 (Aug. 1998).*
A. Fürstner et al., Agnew Chem. Int. Ed., 41: 609-612 (2002).

* cited by examiner

*Primary Examiner*—James O. Wilson
*Assistant Examiner*—Zachary C. Tucker
(74) *Attorney, Agent, or Firm*—Norris McLaughlin & Marcus P.A.

(57) ABSTRACT

A process for the production of compounds Ar—$R^1$ by means of a cross-coupling reaction of an organometallic reagent $R^1$-M with an aromatic or heteroaromatic substrate Ar—X catalyzed by one or several iron salts or iron complexes as catalysts or pre-catalysts, present homogeneously or heterogeneously in the reaction mixture. This new invention exhibits substantial advantages over established cross coupling methodology using palladium- or nickel complexes as the catalysts. Most notable aspects are the fact that (i) expensive and/or toxic nobel metal catalysts are replaced by cheap, stable, commercially available and toxicologically benign iron salts or iron complexes as the catalysts or pre-catalysts, (ii) commercially attractive aryl chlorides as well as various aryl sulfonates can be used as starting materials, (iii) the reaction can be performed under "ligand-free" conditons, and (iv) the reaction times are usually very short.

20 Claims, No Drawings

IRON CATALYZED CROSS COUPLING REACTIONS OF AROMATIC COMPOUNDS

The present invention describes a method for the cross coupling of aromatic compounds with organometallic reagents in the presence of iron salts or iron complexes as the catalysts or pre-catalysts.

Classical cross coupling processes are of utmost importance for modern organic synthesis and have found applications in industrial practice for the production of fine chemicals and biologically active compounds (Review: *Metal-catalyzed Cross-coupling Reactions* (Eds: F. Diederich, P. J. Stang), Wiley-VCH, Weinheim, 1998). In most cases, cross coupling reactions are catalyzed by palladium- or nickel complexes. Despite their versatility and broad scope, however, the need for palladium- and nickel complexes constitutes a significant drawback. Most notable disadvantages are (i) the high cost of the required palladium catalysts, (ii) the potential toxicity of nickel complexes and of possible nickel residues derived thereof in the products formed, (iii) the need for special ligands to render the palladium- or nickel centers sufficiently reactive, and (iv) extended reaction times in many cases. To minimize the costs of production and/or the risk of contamination of the products with potentially toxic residues, considerable efforts have to be made to recover the metal catalysts from the reaction mixtures.

The best substrates for palladium- and nickel catalyzed cross coupling reactions are aryl iodides and aryl bromides. Only recently have special ligands been designed that allow to extend the scope of these methods to aryl chlorides which are usually more attractive substrates due to their lower price; some of these ligands, however, are expensive and sensitive towards oxygen and moisture (C. Dai et al. *J. Am. Chem. Soc.* 2001, 123, 2719–2724; D. W. Old et al. *J. Am. Chem. Soc.* 1998, 120, 9722–9723; J. Huang et al. *J. Am. Chem. Soc.* 1999, 121, 9889–9890; A. Fürstner et al. *Synlett* 2001, 290–292; A. Zapf et al. *Angew. Chem. Int. Ed.* 2000, 39, 4153– 4155; V. P. W. Böhm et al. *J. Organomet. Chem.* 2000, 595, 186–190; X. Bei et al. *J. Org. Chem.* 1999, 64, 6797–6803; J. P. Wolfe et al. *J. Am. Chem. Soc.* 1999, 121, 9550–9561; A. F. Littke et al. *J. Am. Chem. Soc.* 2000, 122, 4020–4028; R. Stürmer *Angew. Chem. Int. Ed.* 1999, 38, 3307–3308). Aryl triflates represent yet another class of suitable starting materials for palladium- or nickel catalyzed cross coupling reactions, whereas less expensive aryl sulfonates, in particular methanesulfonates or p-toluenesulfonates have hardly been used so far for their lack of activity in most cases (V. Percec et al. *J. Org. Chem.* 1995, 60, 1060–1065; Y. Kobayashi et al *Tetrahedron Lett.* 1996, 37, 8531–8534; D. Zim et al. *Org. Lett.* 2001, 3, 3049–3051).

Iron salts have been proposed as catalysts for cross coupling reactions by Kochi et al. as early as 1971 but found little attention in the following decades (M. Tamura et al. *J. Am. Chem. Soc.* 1971, 93, 1487–1489; S. M. Neumann et al. *J. Org. Chem.* 1975, 40, 599–606; R. S. Smith et al. *J. Org. Chem.* 1976, 41, 502–509; J. K. Kochi, *Acc. Chem. Res.* 1974, 7, 351–360). This is partly due to the fact that iron salts in the presence of aryl halides lead to the homo-coupling of Grignard reagents with formation of symmetrical dimers (e.g. phenylmagnesium bromide to biphenyl) rather than to the desired cross coupled products (M. S. Kharasch et al., *J. Am. Chem. Soc.* 1941, 63, 2316–2320). Therefore the scope of iron-catalyzed cross coupling reactions remained limited to reactions of Grignard reagents with alkenyl halides (G. Cahiez et al. *Synthesis* 1998, 1199–1205; G. A. Molander et al. *Tetrahedron Lett.* 1983, 5449–5452; A. Fürstner et al. *Tetrahedron Lett.* 1996, 37, 7009–7012; M. A. Fakhakh et al. *J. Organomet. Chem.* 2001, 624, 131–135; W. Dohle et al., *Synlett* 2001, 1901–1904), alkenyl sulfones (J. L. Fabre et al. *Tetrahedron Lett.* 1982, 23, 2469–2472), carboxylic acid chlorides (V. Fiandanese et al. *Tetrahedron Lett.* 1984, 25, 4805–4808; M. M. Dell'Anna et al., *J. Mol. Catal. A: Chemical* 2000, 161, 239–243) or allylic phosphates (A. Yanagisawa et al. *Synlett* 1991, 513–514; A. Yanagisawa et al., *Tetrahedron* 1991, 50, 6017–6028). Successful iron-catalyzed cross coupling reactions of aromatic compounds such as aryl halides, aryl sulfonates, or aryl phosphates have not been reported.

Surprisingly, however, we have found that the cross-coupling of various types of aromatic substrates with different types of organometallic reagents can be efficiently catalyzed by iron salts or iron complexes under certain conditions specified below (for a preliminary publication during the grace period see: A. Fürstner et al. *Angew. Chem. Int Ed.* 2002, 41, 609–612). This new invention exhibits substantial advantages over established cross coupling methodology. Most notable aspects are the fact that (i) expensive and/or toxic nobel metal catalysts are replaced by cheap, stable, commercially available and toxicologically benign iron salts or iron complexes as the catalysts or pre-catalysts, (ii) commercially attractive aryl chlorides as well as various aryl sulfonates can be used as starting materials, (iii) the reaction can be performed under "ligand-free" conditons, and (iv) the reaction times are usually very short.

The active iron catalyst is formed in situ under reaction conditions from suitable iron precatalysts. All iron compounds of the oxidation states −2, −1, 0, +1, +2, +3 can be used as such precatalysts, including metallic iron or intermetallic iron compounds if used in suitably dispersed form. This includes, but is not restricted to, $FeF_2$, $FeF_2.4H_2O$, $FeF_3$, $FeF_3.3\ H_2O$, $FeCl_2$, $FeCl_2.4\ H_2O$, $FeCl_3$, $FeCl_3.6H_2O$, $FeCl_3(PPh_3)$, $Fe(OEt)_2$, $Fe(OEt)_3$, $FeCl_2.(PPh_3)_2$, $FeCl_2.$(dppe) [dppe=1,2-bis-(diphenylphosphino)-ethane], $Fe(acac)_2$ (acac=acetylacetonate), $Fe(acac)_3$, tris-(trifluoroacetylacetonato)iron (III), tris-(hexafluoroacetylacetonato) iron (III), tris-(dibenzoylmethido)iron (III), tris-(2,2,6,6-tetramethyl-3,5-diheptanedionato)iron (III), $FeBr_2$, $FeBr_3$, $FeI_2$, Fe(II)acetate, Fe(II)oxalate, Fe(II)stearate, Fe(III)citrate.Hydrate, Fe(III)pivalate, Fe(II)-D-gluconate.2 $H_2O$, $Fe(OSO_2C_6H_4Me)_3$, $Fe(OSO_2C_6H_4Me)_3$.Hydrate, $FePO_4$, $Fe(NO_3)_3$, $Fe(NO_3)_3.9\ H_2O$ $Fe(ClO_4)_2$.Hydrate, $FeSO_4$, $FeSO_4$.Hydrate, $Fe_2(SO_4)_3$, $Fe_2(SO_4)_3$.Hydrate, $K_3Fe(CN)_6$, ferrocene, bis(pentamethylcyclopentadienyl)iron, bis(indenyl)iron, Fe(II)phthalocyanin, Fe(III)phthalocyanin chloride, Fe(III)-2,2,6,6-tetramethyl-3,5-heptanedioate, Fe(CO)$_5$, Fe(salen)X [salen=N,N-ethylenebis(salicylidenamidato), X=Cl, Br, I], 5,10,15,20-tetraphenyl-21H,23H-porphin-iron (III) halide, 5,10,15,20-tetrakis(pentafluorophenyl)-21H, 23H-porphin-iron(III) halide, activated Fe (A. V. Kavaliunas et al. *Organometallics* 1983, 2, 377–383; A. Fürstner *Angew. Chem. Int. Ed. Engl.* 1993, 32, 164–189), iron-magnesium intermetallic compounds (L. E. Aleandri et al. *Chem. Mat.* 1995, 7, 1153–1170; B. Bogdanovic et al. *Angew. Chem. Int. Ed.* 2000, 39, 4610–4612). The precatalysts can be used in anhydrous or in hydrated form. Preferred catalysts are those that are soluble or partly soluble in the reaction medium. The catalyst loading can be varied in a wide range, preferably between 0.01 mol % and 20 mol % with regard to the substrates used.

The present invention using said iron precatalyts pertains to the following process:

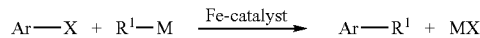

wherein

Ar is any C6–C30 aromatic or heteroaromatic group, with aromatic or heteroaromatic being defined as given in Smith, M. B., March, J. *March's Advanced Organic Chemistry*, 5$^{th}$ Ed., Wiley, N.Y., 2001

X can be selected from halide, sulfonate, phosphonate $R^1$ is any C1–C20 linear or branched alkyl, C3–C20 cycloalkyl, C6–C20 aryl or heteroaryl; said alkyl or aryl groups may be substituted by any substituent which is kinetically inert towards the metal in the reagent $R^1$-M as defined below M is MgZ, CaZ, ZnZ, MnZ Z is any anionic ligand In a preferred embodiment Ar is phenyl, unsubstituted or substituted with 1–5 identical or different substituents chosen from the following list: C1–C10 linear or branched alkyl, C3–C10 cycloalkyl, C1–C10 linear or branched perfluoroalkyl, C2–C10 alkenyl, C2–C10 alkynyl, C6–C20 aryl or heteroaryl, —COOR$^2$, —OR$^3$, —CN, —SR$^4$, —SOR$^5$, —SO$_2$R$^6$, —SO$_2$(OR$^7$), —SO$_2$(NR$^8$R$^9$), —COR$^{10}$, —NR$^{11}$R$^{12}$, —CONR$^{13}$R$^{14}$, —F, —Cl, —SiR$^{15}$R$^{16}$R$^{17}$, —PR$^{18}$R$^{19}$, —P(O)R$^{20}$R$^{21}$, —P(O)(OR$^{22}$)(OR$^{23}$), —P(O)(NR$^{24}$R$^{25}$)(NR$^{26}$R$^{27}$), —NCO, —NCS, —OC(O)OR$^{28}$, —OC(S)OR$^{29}$, —OC(O)NR$^{30}$R$^{31}$, —NR$^{32}$C(O)OR$^{33}$, —NR$^{34}$C(O)NR$^{35}$R$^{36}$, —C(OR$^{37}$)$_2$, —C(OR$^{38}$)(OR$^{39}$), —OC(O)R$^{40}$, —NR$^{41}$C(O)R$^{42}$, —SC(O)R$^{43}$, —N═R$^{44}$, —OSO$_2$R$^{45}$, —NR$^{46}$SO$_2$R$^{47}$, —C(NR$^{48}$)(OR$^{49}$), —N═NR$^{50}$R$^{51}$, —NO$_2$, —C(OR$^{52}$)$_3$, —C(SR$^{53}$)$_2$, —OSiR$^{54}$R$^{55}$R$^{56}$ with $R^2$–$R^{56}$ independently chosen from: H, C1–C10 linear or branched alkyl, C3–C10 cycloalkyl, C1–C10 linear or branched perfluoroalkyl, C2–C10 alkenyl, C2–C10 alkynyl, C6–C20 aryl or heteroaryl; said phenyl ring may be annellated or non-annellated to one or more other rings of any ring size, said other rings being aromatic, heteroaromatic or non-aromatic X is fluoride, chloride, —OSO$_2$R$^{57}$, —OP(O)(OR$^{58}$)(OR$^{59}$) with $R^{57}$–$R^{59}$ being independently chosen from: C1–C10 linear or branched alkyl, C1–C10 cycloalkyl, C1–C10 perfluoroalkyl, C6–C20 aryl or heteroaryl; said alkyl, cycloalkyl, aryl or heteroaryl groups can be substituted with 1–5 identical or different substituents chosen from C1–C6 branched or linear alkyl, C1–C6 perfluoroalkyl, C6–C20 aryl, —F, —CN, $R^1$ is C1–C20 linear or branched alkyl, C3–C20 cycloalkyl, C6–C20 aryl or heteroaryl; said alkyl, cycloalkyl, aryl or heteroaryl group may be substituted or unsubstituted by any substituent which is kinetically inert towards Mg M is MgZ Z is any anionic ligand In another preferred embodiment Ar is a heteroaromatic five-membered or six-membered ring with 1–4 heteroatoms for the five-membered ring or 1–5 heteroatoms for the six-membered ring, respectively, which may be identical or not identical and chosen amongst N, S, O, P; said heteroaromatic five- or six-membered ring may be annellated or not-annelated to one or more other rings of any ring size, said other rings being aromatic, heteroaromatic, or non-aromatic, and can be substituted with 1–5 identical or different substituents chosen from the following list: C1–C10 linear or branched alkyl, C3–C10 cycloalkyl, C1–C10 linear or branched perfluoroalkyl, C2–C10 alkenyl, C2–C10 alkynyl, C6–C20 aryl or heteroaryl, —COOR$^2$, —OR$^3$, —CN, —SR$^4$, —SOR$^5$, —SO$_2$R$^6$, —SO$_2$(OR$^7$), —SO$_2$(NR$^8$R$^9$), —COR$^{10}$, —NR$^{11}$R$^{12}$, —CONR$^{13}$R$^{14}$, —F, —Cl, —SiR$^{15}$R$^{16}$R$^{17}$, —PR$^{18}$R$^{19}$, —P(O)R$^{20}$R$^{21}$, —P(O)(OR$^{22}$)(OR$^{23}$), —P(O)(NR$^{24}$R$^{25}$)(NR$^{26}$R$^{27}$), —NCO, —NCS, —OC(O)OR$^{28}$, —OC(S)OR$^{29}$, —OC(O)NR$^{30}$R$^{31}$, —NR$^{32}$C(O)OR$^{33}$, —NR$^{34}$C(O)NR$^{35}$R$^{36}$, —C(OR$^{37}$)$_2$, —C(OR$^{38}$)(OR$^{39}$), —OC(O)R$^{40}$, —NR$^{41}$C(O)R$^{42}$, —SC(O)R$^{43}$, —N═R$^{44}$, —OSO$_2$R$^{45}$, —NR$^{46}$SO$_2$R$^{47}$, —C(NR$^{48}$)(OR$^{49}$), —N═NR$^{50}$R$^{51}$, —NO$_2$, —C(OR$^{52}$)$_3$, —C(SR$^{53}$)$_2$, —OSiR$^{54}$R$^{55}$R$^{56}$ with $R^2$–$R^{56}$ being independently chosen amongst H, C1–C10 linear or branched alkyl, C3–C10 cycloalkyl, C1–C10 linear or branched perfluoroalkyl, C2–C10 alkenyl, C2–C10 alkynyl, C6–C20 aryl or heteroaryl;

X is fluoride, chloride, —OSO$_2$R$^{57}$, OP(O)(OR$^{58}$)(OR$^{59}$) with $R^{57}$–$R^{59}$ being independently chosen amongst C1–C10 linear or branched alkyl, C1–C10 cycloalkyl, C1–C10 perfluoroalkyl, C6–C20 aryl or heteroaryl; said alkyl, cycloalkyl, aryl or heteroaryl groups can be substituted with 1–5 identical or different substituents chosen from C1–C6 branched or linear alkyl, C1–C6 perfluoroalkyl, C6–C20 aryl, —F, —CN, $R^1$ is C1–C20 linear or branched alkyl, C3–C20 cycloalkyl, C6–C20 aryl or heteroaryl; said alkyl, cycloalkyl, aryl or heteroaryl group may be substituted or unsubstituted by any substitutent which is kinetically inert towards the metal Mg M is MgZ Z is any anionic ligand In a most preferred embodiment X is chloride, methanesulfonate, benzenesulfonate, toluenesulfonate, dimethylbenzenesulfonate, trimethylbenzenesulfonate, triisopropylbenzenesulfonate, fluorobenzenesulfonate, difluorobenzenesulfoante, trifluorobenzenesulfonate, hexafluorobenzenesulfonate, methoxybenzenesulfonate, trifluoromethanesulfonate, or nonafluorobutanesulfonate (nonaflate)

$R^1$ is C1–C20 linear or branched alkyl which may be substituted or unsubstituted by any substitutent which is kinetically inert towards the metal Mg and M is MgZ, wherein Z is fluoride, chloride, bromide, iodide, C1–C20 linear or branched alkyl, C3–C20 cycloalkyl or M is (ZnR$^{60}$R$^{61}$)MgZ wherein $R^{60}$, $R^{61}$ is any C1–C20 linear or branched alkyl, C3–C10 cycloalkyl, C6–C20 aryl or heteroaryl, which may be unsubstituted or substituted by any substitutent which is kinetically inert towards Mg, wherein Z is fluoride, chloride, bromide, iodide The aromatic substrates as defined above may contain more than one group X which may be identical or non-identical and chosen from the lists defined above. If the aromatic substrate contains more than one such group X, the present invention also pertains to:

reactions in which only one of said groups X is selectively replaced during the cross coupling reaction in the presence of iron catalysts or iron precatalysts by an organic residue $R^1$, while the other groups X are preserved in the product formed;

reactions in which all said groups X are replaced during the cross coupling reaction in the presence of iron catalysts or iron precatalysts by the same organic residue $R^1$;

reactions in which said groups X are consecutively replaced during the cross coupling process in the presence of iron catalysts or iron precatalysts with organic residues $R^1$ that are non-identical. This consecutive cross coupling is achieved by consecutive addition of the organometallic reagents $R^1$-M having non-identical residues $R^1$ to the reaction mixture containing said substrate and the iron catalysts or iron precatalysts.

A representative example for an iron-catalyzed cross coupling which simultaneously introduces more than one identical substituent $R^1$ is given in Scheme 1. A representative example for an iron-catalyzed cross coupling which introduces more than one non-identical substituent $R^1$ is given in Schemes 2 and 3. This procedure allows the formation of the musk-odored macrocycle muscopyridine and analogues (H. Schinz et al., *Helv. Chim. Acta* 1946, 29, 1524) by a consecutive iron-catalyzed cross coupling followed by ring closing metathesis (RCM) (A. Fürstner, *Angew, Chem. Int. Ed.* 2000, 39, 3012) and subsequent hydrogenation as shown in Scheme 3.

Scheme 1.

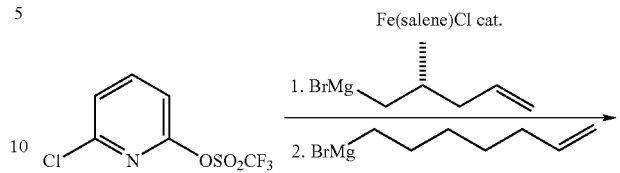

Scheme 2.

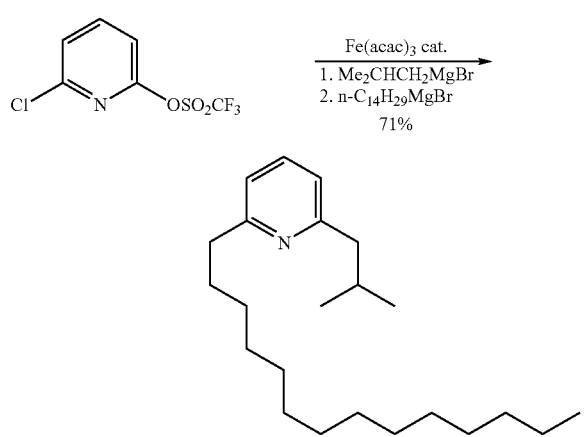

-continued
Scheme 3.

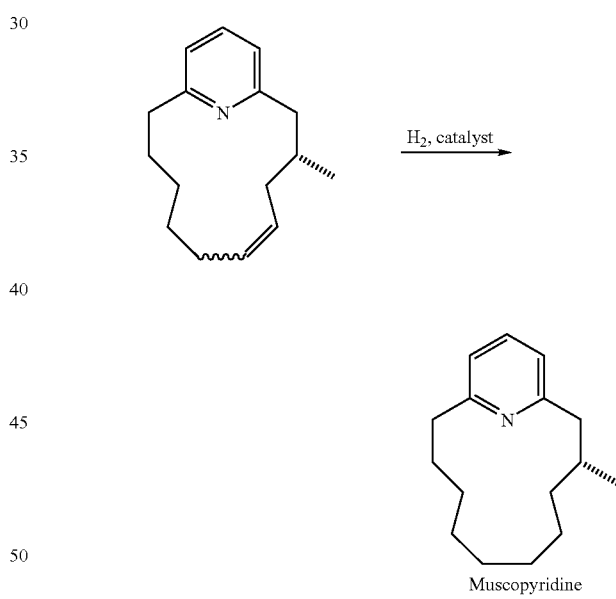

Muscopyridine

The reaction can be performed in any solvent that is inert to the chosen organometallic reagents $R^1$-M as defined above. Prefered solvents are ethereal solvents, hydrocarbon solvents or aprotic dipolar solvents. Possible solvents include, but are not restricted to, diethyl ether, tetrahydrofuran, tetrahydropyran, methyl-tetrahydrofuran, 1,4-dioxane, tert-butyl methyl ether, dibutyl ether, di-isopropyl ether, dimethoxyethane, dimethoxymethane, pentane, hexane, heptane, octane, isooctane, cyclohexane, benzene, toluene, xylene, cymene, petrol ether, decaline, dimethylformamide, dimethylacetamide, dimethylsulfoxide, N-methylpyrrolidinone (NMP), tetramethylurea, sulfolane, diethyl carbonate, 1,3-dimethyltetrahydro-2(1H)-pyrimidinone (DMPU), hexamethylphosphoric acid triamide (HMPA), N,N,N',N'-tetramethylethylenediamine (TMEDA).

In a preferred embodiment, the reaction medium consists of a mixture of two or more solvents, which comprise one or more ethereal or hydrocarbon solvent chosen from: diethyl ether, tetrahydrofuran, tetrahydropyran, methyl-tetrahydrofuran, 1,4-dioxane, tert-butyl methyl ether, dibutyl ether, di-isopropyl ether, dimethoxyethane, dimethoxymethane, pentane, hexane, heptane, octane, isooctane, cyclohexane, benzene, toluene, xylene, cymene, petrol ether, decaline, and one or more aprotic dipolar solvent chosen from: dimethylformamide, dimethylacetamide, dimethylsulfoxide, N-methylpyrrolidinone (NMP), tetramethylurea, sulfolane, diethyl carbonate, 1,3-dimethyltetrahydro-2(1H)-pyrimidinone (DMPU), hexamethylphosphoric acid triamide (HMPA), N,N,N',N'-tetramethylethylenediamine (TMEDA).

The reaction temperature can be varied in a wide range between −78° C. and +120° C. In a preferred embodiment, the reaction is started at temperatures ranging from −10° C. to +30° C. Eventually, heat may evolve during the iron-catalyzed cross coupling, particularly when carried out at larger scale, and appropriate measures must be taken to control the reaction temperature to avoid any risks associated with such formation of heat. One possibility consists in the slow addition of the organometallic reagent $R^1$-M to the reaction mixture which may additionally be cooled.

The scope of the iron catalyzed cross coupling is illustrated by—but by no means restricted to—the examples compiled in Tables 1–3 and in the Experimental Section. Products accessible by said iron catalyzed cross coupling process can be used as, or may serve as precursors for detergents, agrochemicals, pharmaceutically active compounds for use in human or veterinary medicine, dyes, pheromones, lubricants, perfume ingredients, aroma ingredients.

TABLE 1

Screening of different substrates in the iron catalyzed cross coupling reaction depicted below:

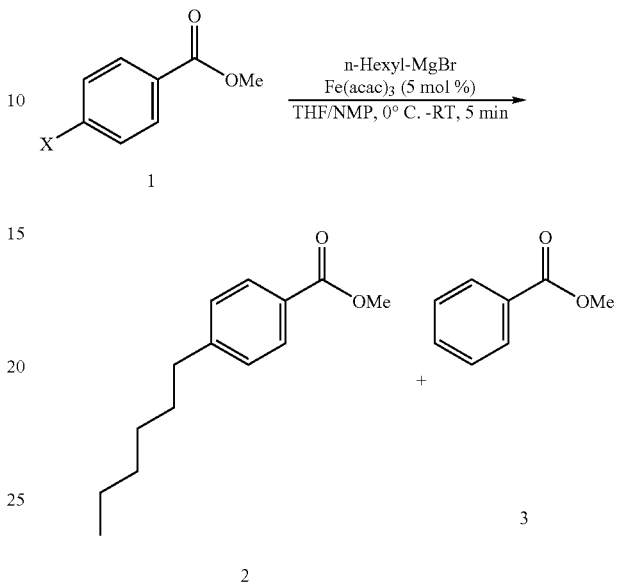

| | | Yield (GC, %) | |
|---|---|---|---|
| Nr | X | 2 | 3 |
| 1 | I | 27 | 46 |
| 2 | Br | 38 | 50 |
| 3 | Cl | >95 | — |
| 4 | $OSO_2CF_3$ | >95 | — |
| 5 | $OSO_2C_6H_4Me$ | >95 | — |

TABLE 2

Screening of different iron precatalysts (5 mol %) and of different nucleophiles in cross coupling reactions with two representative aryl chlorides.

| Nr | Ar—Cl | R—M | Fe-precatalyst | Ar—R (%)[a] |
|---|---|---|---|---|
| 1 | 2-chloropyridine | n-$C_6H_{13}$MgBr | Fe(acac)$_2$ | 90 |
| 2 | | n-$C_6H_{13}$MgBr | Fe(acac)$_3$ | 91 |
| 3 | | n-$C_6H_{13}$MgBr | FeCl$_3$ | 88 |
| 4 | | n-$C_6H_{13}$MgBr | Fe(salen)Cl[c] | 96 |
| 5 | methyl 4-chlorobenzoate | $C_2H_5$MgBr | Fe(acac)$_3$ | >95 |
| 6 | | n-$C_6H_{13}$MgBr | Fe(acac)$_3$ | >95 |
| 7 | | n-$C_6H_{13}$MgBr | FeCl$_2$ | >95 |
| 8 | | n-$C_{14}H_{29}$MgBr | Fe(acac)$_3$ | >95 |
| 9 | | i-$C_3H_7$MgBr | Fe(salen)Cl[c] | 59 |
| 10 | | hexenyl-MgBr | Fe(acac)$_3$ | 91[b] |

TABLE 2-continued

Screening of different iron precatalysts (5 mol %) and of different nucleophiles in cross coupling reactions with two representative aryl chlorides.

| Nr | Ar—Cl | R—M | Fe-precatalyst | Ar—R (%)[a] |
|---|---|---|---|---|
| 11 | |  MOMO~~~~~~~~~~MgBr | Fe(acac)$_3$ | 88[b] |
| 12 | | 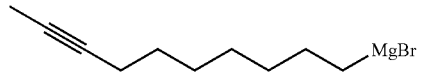 ≡~~~~~~~~MgBr | Fe(acac)$_3$ | 85[b] |
| 13 | | H$_2$C=CHMgBr | Fe(acac)$_3$ | 0 |
| 14 | | H$_2$C=CHCH$_2$MgBr | Fe(acac)$_3$ | 0 |
| 15 | | C$_6$H$_5$MgBr | Fe(acac)$_3$ | 28 |
| 16 | | Et$_3$ZnMgBr | Fe(acac)$_3$ | 93 |

[a]GC yields unless stated otherwise;
[b]isolated yields;
[c]salen = N,N-ethylenebis(salicylideneamidato)

TABLE 3

Iron catalyzed cross coupling reactions of different Grignard reagents with representative aryl chlorides, triflates (OTf) and tosylates (OTs). Isolated yields of the corresponding cross coupling products are given.

| Nr | Ar—X | R—MgX | X = Cl | X = OTf | X = OTs |
|---|---|---|---|---|---|
| 1 | 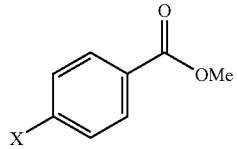 | n-C$_6$H$_{13}$MgBr | 91% | 87% | 83% |
| 2 | 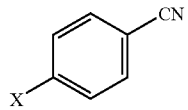 | n-C$_6$H$_{13}$MgBr | 91% | 80% | 74% |
| 3 | 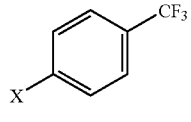 | n-C$_{14}$H$_{29}$MgBr | 94% | 72% | 75% |
| 4 | 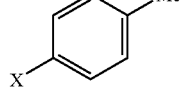 | n-C$_{14}$H$_{29}$MgBr | 0% | 81% | 0% |
| 5 | 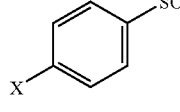 | n-C$_6$H$_{13}$MgBr | 85% (R = OiPr) | | |
| 6 | | | 94% (R = N(iPr)$_2$) | | |
| 7 | 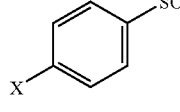 | n-C$_{14}$H$_{29}$MgBr | 0% | 90% | 0% |
| 8 | 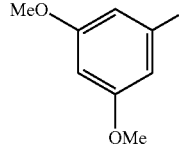 | n-C$_{14}$H$_{29}$MgBr | | 81% | |

TABLE 3-continued

Iron catalyzed cross coupling reactions of different Grignard reagents with representative aryl chlorides, triflates (OTf) and tosylates (OTs). Isolated yields of the corresponding cross coupling products are given.

| Nr | Ar—X | R—MgX | X = Cl | X = OTf | X = OTs |
|---|---|---|---|---|---|
| 9 | 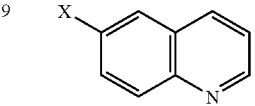 | n-C$_{14}$H$_{29}$MgBr | 92% | 74% | 82% |
| 10 | 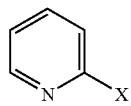 | n-C$_{14}$H$_{29}$MgBr | 81% | | |
| 11 | 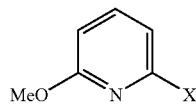 | n-C$_{14}$H$_{29}$MgBr | 95% | | |
| 12 | | (CH$_3$)$_2$CHMgBr | 56% | | |
| 13 | 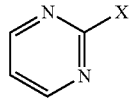 | n-C$_{14}$H$_{29}$MgBr | 93% | | |
| 14 | 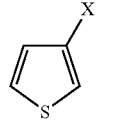 | n-C$_{14}$H$_{29}$MgBr | 41% | | |
| 15 | 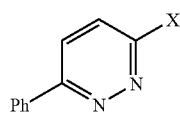 | n-C$_{14}$H$_{29}$MgBr | 68% | | |
| 16 | 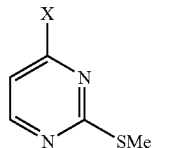 | n-C$_{14}$H$_{29}$MgBr | 89% | | |
| 17 | | PhMgBr | 53% | | |
| 18 | 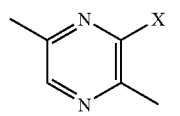 | n-C$_{14}$H$_{29}$MgBr | 94% | | |
| 19 | | PhMgBr | 64% | | |
| 20 | 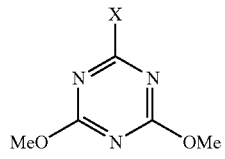 | n-C$_{14}$H$_{29}$MgBr | 84% | | |
| 21 | | PhMgBr | 63% | | |
| 22 | 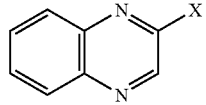 | n-C$_{14}$H$_{29}$MgBr | 95% | | |
| 23 | | PhMgBr | 73% | | |
| 24 | 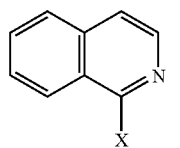 | n-C$_{14}$H$_{29}$MgBr | 95% | | |
| 25 | | PhMgBr | 57% | | |

TABLE 3-continued
Iron catalyzed cross coupling reactions of different Grignard reagents with representative aryl chlorides, triflates (OTf) and tosylates (OTs). Isolated yields of the corresponding cross coupling products are given.
| Nr | Ar—X | R—MgX | X = Cl | X = OTf | X = OTs |
|---|---|---|---|---|---|
| 26 | 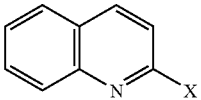 | PhMgBr | 71% | | |
| 27 | 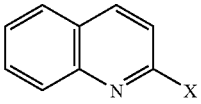 | 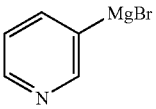 | 60% | | |
| 28 | 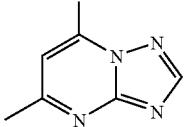 | n-C$_{14}$H$_{29}$MgBr | 67% | | |
| 29 | 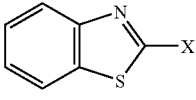 | n-C$_{14}$H$_{29}$MgBr | 68% | | |
| 30 | 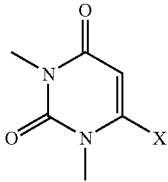 | n-C$_{14}$H$_{29}$MgBr | 60% | | |
| 31 | 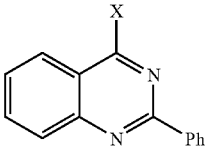 | n-C$_{14}$H$_{29}$MgBr | 84% | | |
| 32 | | PhMgBr | 66% | | |
| 33 | 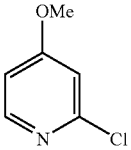 | 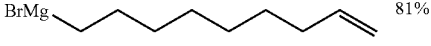 | 81% | | |
| 34 | 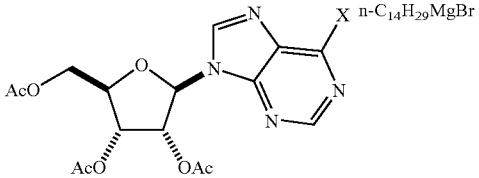 | n-C$_{14}$H$_{29}$MgBr | 56% | | |

The examples specified hereafter describe prototypical cross coupling reactions using iron salts or iron complexes as pre-catalysts under preferred conditions. However, said examples should by no means limit the scope, the scope of application, or the advantages of the present invention.

EXAMPLE 1

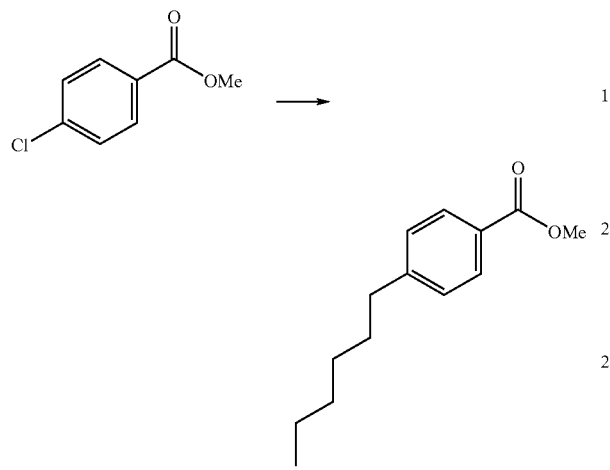

A flame-dried two-necked flask is charged under argon with 4-chlorobenzoic acid methyl ester (1.00 g, 5.86 mmol), Fe(acac)$_3$ (103 mg, 0.29 mmol), THF (35 mL) and N-methylpyrrolidone (NMP, 3.3 mL). A solution of n-hexylmagnesium bromide (2M in Et$_2$O, 3.5 mL, 7.00 mmol) is added via syringe to the resulting red solution, causing an immediate color change to dark brown and finally to violet. The resulting mixture is stirred for 5–10 min, the reaction is diluted with Et$_2$O and is carefully quenched upon addition of aq. HCl (1M, ca. 10 mL). Standard extractive work-up followed by flash chromatography of the crude product (hexanes/ethyl acetate, 30/1) provides the cross coupling product as a colorless syrup (1.24 g, 91%). $^1$H NMR (300 MHz, CDCl$_3$): δ =7.90 (d, J=8.3 Hz, 2H), 7.19 (d, J=8.4 Hz, 2H), 3.84 (s, 3H), 2.59 (t, J=7.7 Hz, 2H), 1.57 (m, 2H), 1.21–1.29 (m, 6H), 0.84 (t, J=6.9 Hz, 3H); $^{13}$C NMR (75 MHz, CDCl$_3$): δ =167.1, 148.4, 129.2, 128.7, 51.8, 35.9, 31.2, 31.0, 28.9, 22.5, 13.9; IR: ν=1724 cm$^{-1}$; MS (EI): m/z (rel. intensity): 220 (50, [M$^+$]), 189 (39), 150 (100), 91 (54), 43 (17).

EXAMPLE 2

Use of FeCl$_2$ as the Precatalyst

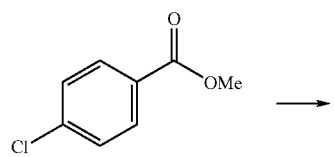

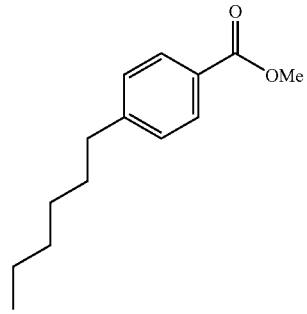

A flame-dried two-necked flask is charged under argon with 4-chlorobenzoic acid methyl ester (0.5 g, 2.93 mmol), FeCl$_2$ (19 mg, 0.15 mmol), THF (7 mL) and N-methylpyrrolidone (NMP, 1 mL). A solution of n-hexylmagnesium bromide (2M in Et$_2$O, 1.9 mL, 3.8 mmol) is added via syringe to the resulting red solution, causing an immediate color change to dark brown and finally to violet. The resulting mixture is stirred for 5 min. Work-up as described above provides 4-hexylbenzoic acid methyl ester as a colorless syrup (90%). The spectroscopic and analytical data are identical to those compiled above.

EXAMPLE 3

Cross Coupling of an Aryl Tosylate as the Substrate

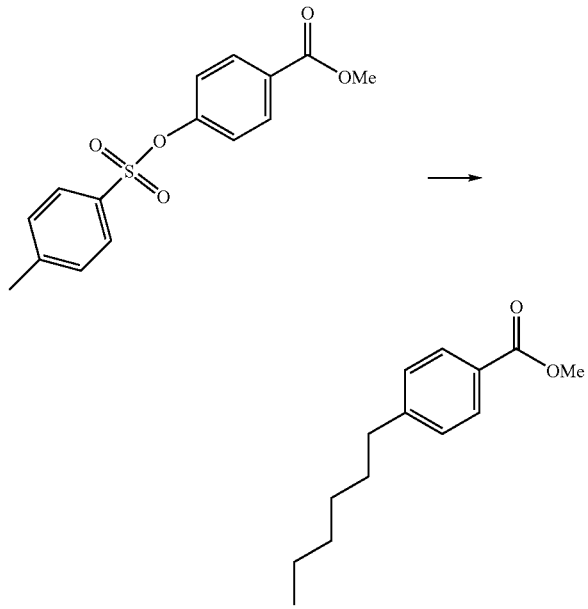

A flame-dried two-necked flask is charged under argon with 4-(4-methylbenzenesulfonyloxy)benzoic acid methyl ester (0.50 g, 1.63 mmol), Fe(acac)$_3$ (29 mg, 0.08 mmol), THF (10 mL) and N-methylpyrrolidone (NMP, 0.95 mL). A solution of n-hexylmagnesium bromide (2M in Et$_2$O, 1 mL, 2 mmol) is added via syringe to the resulting red solution, causing an immediate color change to dark brown and finally to violet. The resulting mixture is stirred for 5 min, the reaction is diluted with Et$_2$O and is carefully quenched upon addition of aq. HCl (1M, ca. 10 mL). Work-up followed by flash chromatography of the crude product as described above provides 4-hexylbenzoic acid methyl ester as a colorless syrup (298 mg, 83%). The spectroscopic and analytical data are identical to those compiled above.

EXAMPLE 4

Cross Coupling of an Aryl Triflate as the Substrate

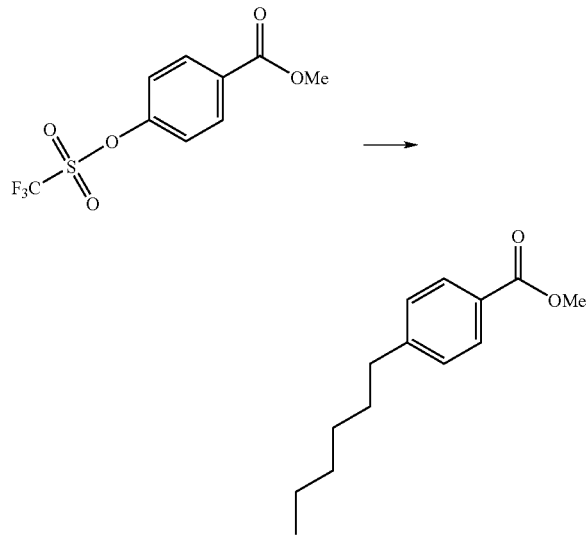

A flame-dried two-necked flask is charged under argon with 4-(trifluoromethylsulfonyloxy)benzoic acid methyl ester (760 mg, 2.66 mmol), Fe(acac)$_3$ (47 mg, 0.13 mmol), THF (30 mL) and N-methylpyrrolidone (NMP, 1.7 mL). A solution of n-hexylmagnesium bromide (2M in Et$_2$O, 1.7 mL, 3.4 mmol) is added via syringe to the resulting red solution, causing an immediate color change to dark brown and finally to violet. The resulting mixture is stirred for 5 min, the reaction is diluted with Et$_2$O and is carefully quenched upon addition of aq. HCl (1M, ca. 10 mL). Work-up followed by flash chromatography of the crude product as described above provides 4-hexylbenzoic acid methyl ester as a colorless syrup (540 mg, 93%). The spectroscopic and analytical data are identical to those compiled above.

EXAMPLE 5

Cross Coupling at Low Temperature

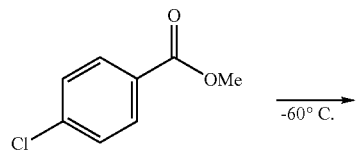

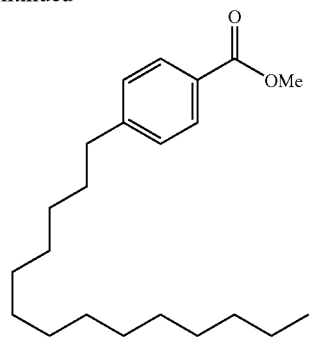

To a solution of methyl 4-chlorobenzoate (300 mg, 1.76 mmol) and Fe(acac)$_3$ (71 mg, 0.2 mmol) in THF (7 mL) and NMP (1.1 mL) at −60° C. is added a solution of C$_{14}$H$_{29}$MgCl (1M in THF, 2.3 mL). The mixture immediately turns black and becomes viscous after 3 min. Work-up as described above provides methyl 4-(tetradecyl)benzoate as a low-melting solid (92%). Mp=28–29° C. $^1$H NMR (300 MHz, CDCl$_3$): δ 7.92 (dd, 2H, J=6.5, 1.8 Hz), 7.21 (dd, 2H, J=6.4, 1.7 Hz), 3.87 (s, 3H), 2.63 (t, 2H, J=7.7 Hz), 1.60 (m, 2H), 1.38–1.06 (m, 24H), 0.86 (t, 3H, J=6.7 Hz). $^{13}$C NMR (75 MHz, CDCl$_3$): δ 167.6, 148.9, 130.0, 128.8, 128.0, 52.3, 36.4, 32.3, 31.5, 30.09, 30.07, 30.05, 30.00. 29.95, 29.9, 29.8, 29.7, 23.1, 14.5. IR: 3091, 3061, 3031, 2925, 2854, 1726, 1611, 1574, 1510, 1466, 1435, 1415, 1377, 1309, 1277, 1191, 1178, 1109, 1021, 970, 854, 763, 722, 704 cm$^{-1}$. MS m/z (rel. intensity) 332 (100, [M$^+$]), 301 (1), 163 (34), 150 (60), 149 (29).

EXAMPLE 6

Simultaneous Substitution of Two Different Leaving Groups

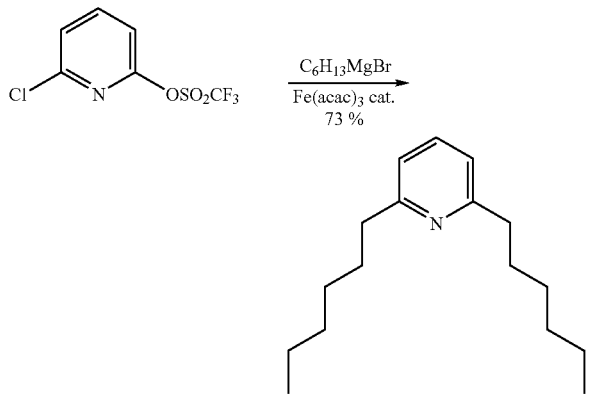

A solution of n-hexylmagnesium bromide (2M in Et$_2$O, 3.3 mL) is added to a solution of 6-chloro-2-(trifluoromethanesulfonyloxy)pyridine (435 mg, 1.66 mmol) in THF (7 mL) and NMP (0.5 mL) at 0° C. The reaction mixture turns black and GC inspection indicates quantitative conversion of the substrate after 5 min reacion time. For work-up, the mixture is diluted with Et$_2$O (20 mL) and quenched with brine (20 mL), the aqueous phase is repeatedly extracted with Et$_2$O, the combined organic layers are dried over Na$_2$SO$_4$ and evaporated, and the residue is purified by flash chromatography (hexanes/ethyl acetate, 15/1) to afford 2,6-di(hexyl)pyridine as a colorless liquid (301 mg, 73%). $^1$H NMR (300 MHz, CDCl$_3$): δ 7.47 (t, J=7.7 Hz, 1H), 6.93 (d, J=7.7 Hz, 2H), 2.70 (t, J=7.8 Hz, 4H), 1.68 (m, 4H), 1.32 (m, 12H), 0.88 (t, J=6.5 Hz, 6H). $^{13}$C NMR (75 MHz, CDCl$_3$): δ 161.9, 136.2, 119.5, 38.5, 31.8, 30.0, 29.1, 22.7, 13.9. IR: 3060, 2955, 2926, 2871, 2856, 1590, 1577, 1456, 1378, 750 cm$^{-1}$. MS m/z (rel. intensity) 247 (5, [M$^+$]), 218 (7), 204 (22), 190 (23), 177 (100), 134 (12), 120 (44), 107 (15). HR-MS (C$_{17}$H$_{29}$N) calcd. 247.229999; found 247.229778.

EXAMPLE 7

Consecutive Cross Coupling with Two Different Grignard Reagents

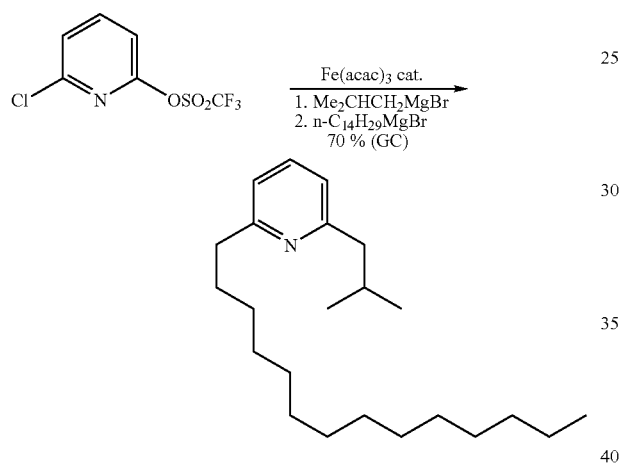

To a solution of 6-chloro-2-(trifluoromethanesulfonyloxy)pyridine (508 mg, 1.94 mmol) and Fe(acac)$_3$ (34 mg, 0.096 mmol) in THF (8 mL) and NMP (2.3 mL) at 0° C. is slowly added a solution of isobutylmagnesium bromide (2M in Et$_2$O, 1.1 mL, 2.2 mmol) causing a color change to yellow-brown. After stirring for 3 min at that temperature, a solution of C$_{14}$H$_{29}$MgCl (1M in THF, 2.3 mL, 2.3 mmol) is introduced via syringe causing an immediate color change to black-violet. After stirring for 5 min, an additional portion of Fe(acac)$_3$ (20 mg, 0.057 mmol) and C$_{14}$H$_{29}$MgCl (1M in THF, 0.5 mL, 0.5 mmol) are added consecutively and the resulting mixture is stirred for another 15 min. Quenching of the reaction with brine followed by a standard extractive work up and flash chromatography (hexanes/ethyl acetate, 20/1) affords 2-(isobutyl)-6-(tetradecyl)pyridine as a colorless liquid (449 mg, 71%). $^1$H NMR (300 MHz, CDCl$_3$): δ 7.47 (t, J=8.3 Hz, 1H), 6.94 (d, J=7.6 Hz, 1H), 6.90 (d, J=7.6 Hz, 1H), 2.71 (t, J=7.7 Hz, 2H), 2.58 (d, J=7.2 Hz, 2H), 2.07 (m, J=6.8 Hz, 1H), 1.68 (m, 2H), 1.20–1.35 (m, 22H), 0.87–0.92 (m, 9H). $^{13}$C NMR (75 MHz, CDCl$_3$): 161.9, 160.9, 136.0, 120.4, 119.6, 47.6, 38.5, 32.0, 30.1, 29.80, 29.78, 29.75, 29.71, 29.6, 29.48, 29.47, 29.2, 22.8, 22.3, 13.9. MS m/z (rel. intensity) 331 (11, [M$^+$], 316 (9), 289 (31), 176 (11), 162 (16), 149 (100), 120 (24), 107 (23).

EXAMPLE 8

Cross Coupling with a Zincate as the Nucleophile

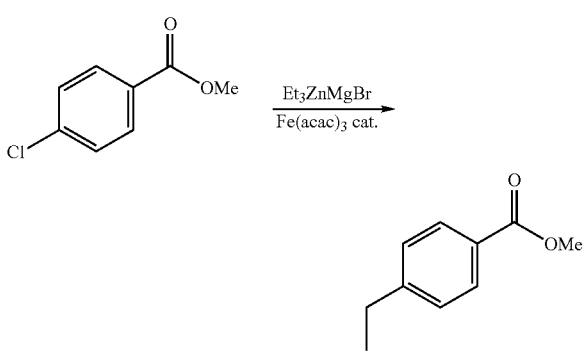

A solution of EtMgBr (3 M in Et$_2$O, 0.9 mL) is added to a solution of Et$_2$Zn (3 M in toluene, 1 mL) at −78° C. After stirring for 15 min, the resulting cold solution of the zincate is added dropwise to a solution of methyl 4-chlorobenzoate (354 mg, 2.10 mmol) and Fe(acac)$_3$ (36 mg, 0.1 mmol) in THF (6 mL) and NMP (0.5 mL) at 0° C. causing a spontaneous color change from yellow to brown-black. Standard extractive work up followed by flash chromatography affords 4-ethylbenzoic acid methyl ester (93%) the analytical and spectroscopic data of which are identical to those of a commercial sample.

EXAMPLE 9

Iron-Salen Catalyzed Cross Coupling of a Secondary Grignard Reagent

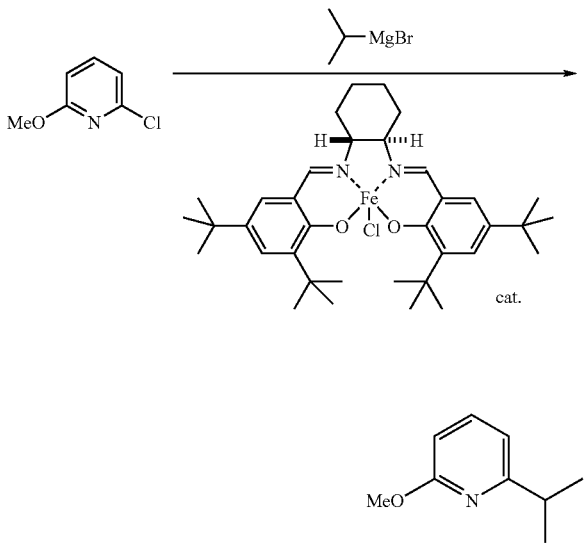

A flame-dried two-necked flask is charged under argon with 2-chloro-6-methoxypyridine (420 mg, 2.93 mmol), the shown Fe(salen)Cl complex (93 mg, 0.147 mmol), THF (10 mL) and N-methylpyrrolidone (NMP, 1.8 mL). A solution of isopropylmagnesium bromide (2M in Et$_2$O, 1.9 mL, 3.8 mmol) is added at ambient temperature via syringe to the resulting red solution, causing an immediate color change to dark brown and finally to violet. The resulting mixture is stirred for 10 min, the reaction is diluted with Et$_2$O and is carefully quenched upon addition of brine. A standard extractive work-up followed by flash chromatography (hexanes) of the crude product provides the cross coupling product as a colorless liquid (246 mg, 56%). $^1$H NMR (300 MHz, CDCl$_3$): δ 7.48 (dd, J=8.0, 7.4 Hz, 1H), 6.73 (d, J=7.2 Hz, 1H), 6.52 (d, J=8.3 Hz, 1H), 3.91 (s, 3H), 2.93 (hept., 1H), 1.27 (d, J=6.9 Hz, 6H). $^{13}$C NMR (75 MHz, CDCl$_3$): δ 165.3, 163.1, 138.8, 112.9, 107.4, 52.9, 35.9, 22.2. IR: 3066, 2965, 2907, 2871, 1595, 1580, 1464, 1414, 1288, 1255, 1031, 801 cm$^{-1}$. MS m/z (rel. intensity) 151 (41, [M$^+$]), 150 (67), 136 (100), 121 (19), 104 (21), 93 (11).

EXAMPLE 10

Cross Coupling of an Aryl Grignard Reagent

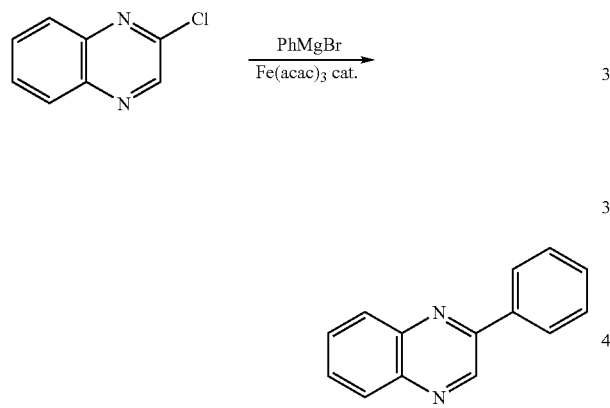

A flame-dried two necked round bottom flask is charged under Ar with 2-chloroquinoxaline (300 mg, 1.82 mmol), Fe(acac)$_3$ (32 mg, 0.09 mmol) and THF (10 mL), and the mixture was cooled to −30° C. A solution of phenylmagnesium bromide (1M in THF, 4.2 mL, 4.2 mmol) is added via syringe to the resulting red solution, causing an immediate color change to dark brown/black. The resulting mixture is stirred for 30 min time while the temperature was allowed to reach −5° C., it was then diluted with Et$_2$O and carefully quenched with saturated NaCl. Standard extractive work-up followed by column chromatography (hexanes:EtOAc 13:1) provides the cross-coupling product as a white solid (263 mg, 70%): mp=73–75° C. $^1$H NMR (400 MHz, CDCl$_3$) δ 9.32 (s, 1H), 8.21–8.10 (m, 4H), 7.79–7.71 (m, 2H), 7.58–7.49 (m, 3H); $^{13}$C NMR (100 MHz, CDCl$_3$) (DEPT) δ 151.79 (C), 143.26 (CH), 142.27 (C), 141.54 (C), 136.75 (C), 130.20 (CH), 130.12 (CH), 129.59 (CH), 129.47 (CH), 129.09 (CH), 127.51 (CH). IR: υ (cm$^{-1}$, KBr) 3061, 1545, 1488, 1486, 1313, 769, 750, 687. MS (EI): m/z (rel. intensity): 206 (100, [M$^+$]), 179 (36), 152 (5), 103 (12), 76 (19), 50 (9).

EXAMPLE 11

Cross Coupling of an Aryl Grignard Reagent Using an Iron-Salen Precatalyst

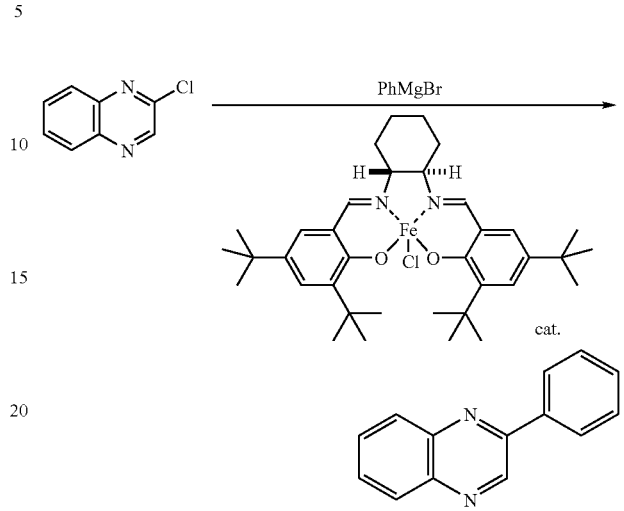

A flame-dried two necked round bottom flask is charged under Ar with 2-chloroquinoxaline (300 mg, 1.82 mmol), the shown Fe(salen)Cl (29 mg, 0.09 mmol) and THF (10 mL), and the mixture was cooled to −30° C. A solution of phenylmagnesium bromide (1M in THF; 4.2 mL, 4.2 mmol) is added via syringe to the resulting red solution, causing an immediate color change to dark brown/black. The resulting mixture is stirred for 10 min, is then diluted with Et$_2$O and carefully quenched with saturated NaCl. Standard extractive work-up followed by column chromatography (hexanes: EtOAc 13:1) provides the cross-coupling product as a white solid (275 mg, 73%). The analytical and spectroscopic data are identical to those compiled above.

EXAMPLE 12

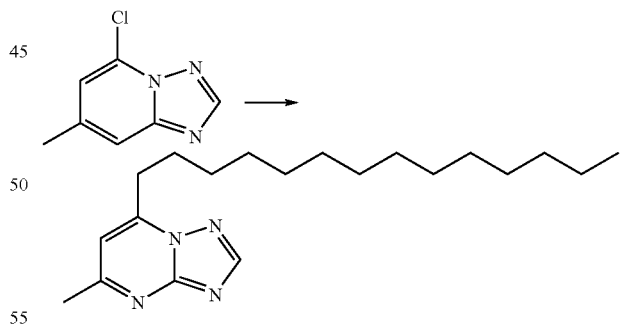

A flame-dried two necked round bottom flask is charged under Ar with the shown aryl chloride (300 mg, 1.81 mmol), Fe(acac)$_3$ (32 mg, 0.09 mmol), THF (8 mL) and NMP (1.13 mL, 11.76 mmol). A solution of n-tetradecylmagnesium bromide (1M in THF, 2.3 mL, 2.3 mmol) is added via syringe to the resulting red solution, causing an immediate color change to dark brown. The resulting mixture is stirred for 5–10 min, diluted with EtOAc and carefully quenched with saturated NH$_4$Cl. The aqueous layer was then reextracted with CHCl$_3$. Standard extractive work-up, followed by column chromatography (hexanes:EtOAc 1:1 containing 5% CHCl₃) provides the cross-coupling product as a white solid (403 mg, 67%). mp=64–66° C. ¹H NMR (400 MHz, CDCl₃) δ 8.41 (s, 1H), 6.81 (s, 1H), 3.14 (t, J=7.7 Hz, 2H), 2.68 (s, 3H), 1.86 (m, 2H), 1.47–1.26 (m, 22H), 0.88 (m, 3H); ¹³C NMR (100 MHz, CDCl₃) (DEPT) δ 164.68 (C), 155.19 (CH), 155.11 (C), 150.54 (C), 109.23 (CH), 31.75 (CH₂), 30.29 (CH₂), 29.51 (CH₂), 29.48 (CH₂), 29.46 (CH₂), 29.41 (CH₂), 29.27 (CH₂), 29.18 (CH₂), 29.09 (CH₂), 29.06 (CH₂), 25.95 (CH₂), 24.90 (CH₃), 22.51 (CH₂), 13.93 (CH₃); IR: υ (cm⁻¹) 3109, 2955, 2924, 2852, 1617, 1543, 1460, 1293; MS (EI): m/z (rel. intensity): 330 (21, [M⁺]), 301 (4), 161 (41), 148 (100). Anal. Calcd. for C₂₀H₃₄N₄: C, 72.68; H, 10.38. Found: C, 72.49; H, 10.31.

EXAMPLE 13

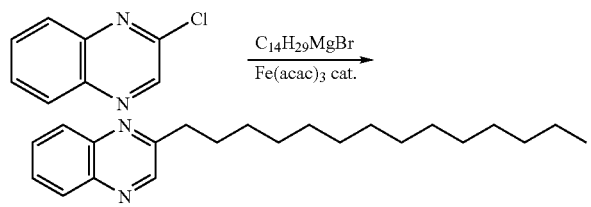

A flame-dried two necked round bottom flask is charged under Ar with 2-chloroquinoxaline (500 mg, 3.06 mmol), Fe(acac)₃ (54 mg, 0.15 mmol), THF (15 mL) and NMP (1.9 mL, 19.8 mmol). A solution of n-tetradecylmagnesium bromide (1M in THF, 4.0 mL, 4.0 mmol) is added via syringe to the resulting red solution, causing an immediate color change to dark brown. The resulting mixture is stirred for 5–10 min, diluted with Et₂O and carefully quenched with saturated NaCl. Standard extractive work-up followed by column chromatography (hexanes:EtOAc 10:1) provides the cross-coupling product as a white solid (950 mg, 95%): mp=25–27° C. ¹H NMR (400 MHz, CDCl₃) δ 8.73 (s, 1H), 8.08–8.02 (m, 2H), 7.75–7.67 (m, 2H), 3.00 (t, J=7.6 Hz, 2H), 1.84 (m, 2H), 1.44–1.22 (m, 22H), 0.87 (m, 3H); ¹³C NMR (100 MHz, CDCl₃) (DEPT) δ 157.68 (C), 145.80 (CH), 142.20 (C), 141.21 (C), 129.83 (CH), 129.15 (CH), 128.85 (CH), 128.82 (CH), 36.51 (CH₂), 31.89 (CH₂), 29.65 (CH₂), 29.63 (CH₂), 29.61 (CH₂), 29.58 (CH₂), 29.48 (CH₂), 29.42 (CH₂), 29.40 (CH₂), 29.31 (CH₂), 22.65 (CH₂), 14.06 (CH₃); IR: υ (cm⁻¹) 3087, 2916, 2848, 1563, 1492, 1464, 765; MS (EI): m/z (rel. intensity): 326 (16, [M⁺]), 157 (11), 144 (100), 117 (2), 43 (4). Anal. Calcd. for C₂₂H₃₄N₂: C, 80.93; H, 10.50. Found: C, 80.86; H, 10.54.

EXAMPLE 14

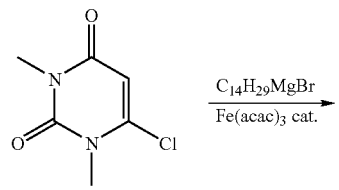

-continued

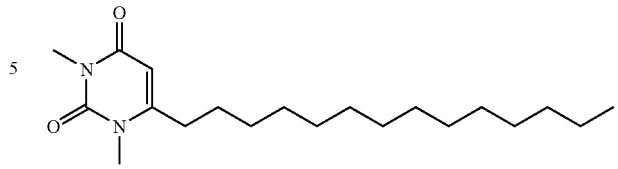

To a solution of Fe(acac)₃ (23 mg, 0.065 mmol) and NMP (0.8 mL, 8.4 mmol) in 3 mL of THF under Ar, n-tetradecylmagnesium bromide (1M in THF, 0.4 mL, 0.4 mmol) is added causing the reaction color to change from red to dark brown. Then a solution 1,3-dimethyl-6-chlorouracil (200 mg, 1.29 mmol) in THF (3 mL) is added via cannula followed by the rest of the n-tetradecylmagnesium bromide (1M in THF, 1.3 mL, 1.3 mmol). The temperature of the resulting mixture rises as a consequence of the addition of the Grignard. The resulting mixture is stirred for 5–10 min in which the color of the reaction fades to yellow. Dilution with Et₂O, quenching of the reaction with brine followed by a standard extractive work-up and flash chromatography (hexanes:EtOAc 6:1) provides the cross-coupling product as a white solid (259 mg, 60%). mp=59–60° C. ¹H NMR (400 MHz, CDCl₃) δ 5.52 (s, 1H), 3.34 (bs, 3H), 3.27 (bs, 3H), 2.41 (m, 2H), 1.54 (m, 2H), 1.11–1.20 (m, 22H), 0.82 (m, 3H); ¹³C NMR (100 MHz, CDCl₃) (DEPT) δ 162.49 (C), 155.05 (C), 152.60 (C), 99.91 (CH), 32.50 (CH₂), 31.77 (CH₂), 31.17 (CH₃), 29.50 (CH₂), 29.42 (CH₂), 29.30 (CH₂), 29.21 (CH₂), 29.12 (CH₂), 28.94 (CH₂), 27.75 (CH₃), 26.97 (CH₂), 22.54 (CH₂), 13.96 (CH₃); IR: υ (cm⁻¹) 2924, 2847, 1706, 1665, 1467; MS (EI): m/z (rel. intensity): 336 (15, [M⁺]), 167 (31), 154 (100), 127 (4), 97 (8). Anal Calcd. for C₂₀H₃₆N₂O₂: C, 71.38; H, 10.78. Found: C, 71.24; H, 10.64.

EXAMPLE 15

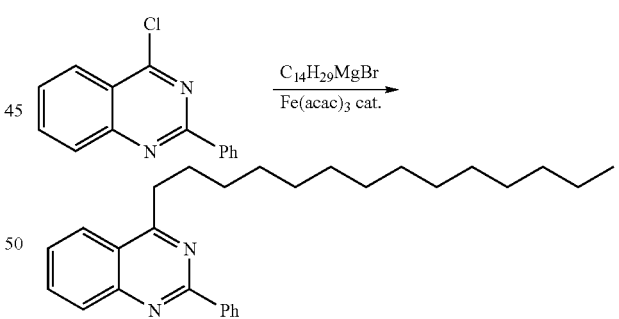

A flame-dried two necked round bottom flask is charged under Ar with 4-chloro-2-phenylquinazoline (500 mg, 2.08 mmol), Fe(acac)₃ (37 mg, 0.10 mmol), THF (15 mL) and NMP (1.3 mL, 13.5 mmol). A solution of n-tetradecylmagnesium bromide (1M in THF, 2.7 mL, 2.7 mmol) is added via syringe to the resulting red solution, causing an immediate color change to dark brown. The resulting mixture is stirred for 5–10 min, diluted with Et₂O and carefully quenched with saturated NaCl. Standard extractive work-up followed by column chromatography (hexanes:EtOAc 10:1) provides the cross-coupling product as a white solid (701 mg, 84%). mp=54–56° C. ¹H NMR (300 MHz, CDCl₃) δ 8.70 (m, 2H), 8.1 (d, J=8.6 Hz, 2H), 7.84 (m, 1H), 7.59–7.47

(m, 4H), 3.32 (t, J=7.6 Hz, 2H), 2.00 (m, 2H), 1.59–1.22 (m, 22H), 0.92 (m, 3H); $^{13}$C NMR (100 MHz, CDCl$_3$) (DEPT) δ 171.38 (C), 160.01 (C), 150.66 (C), 138.47 (CH), 133.17 (CH), 130.25 (CH), 129.35 (CH), 128.55 (CH), 128.42 (CH), 126.59 (CH), 124.50 (CH), 122.48 (CH), 34.51 (CH$_2$), 31.91 (CH$_2$), 29.67 (CH$_2$), 29.58 (CH$_2$), 29.51 (CH$_2$), 29.35 (CH$_2$), 28.48 (CH$_2$), 22.67 (CH$_2$), 14.10 (CH$_3$); IR: υ (cm$^{-1}$) 3067, 2913, 2850,1616, 1549, 1345, 761, 703.

EXAMPLE 16

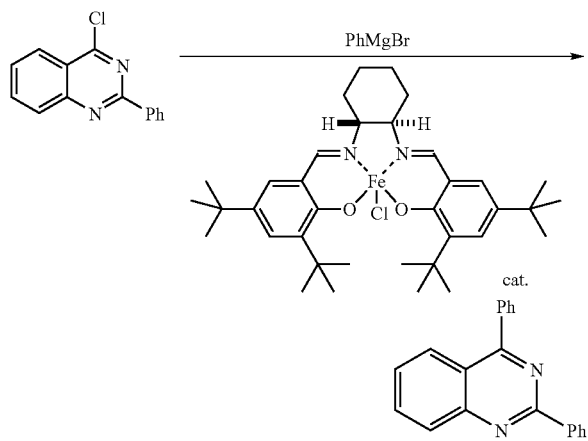

A flame-dried two necked round bottom flask is charged under Ar with 4-chloro-2-phenylquinazoline (500 mg, 2.08 mmol), the shown Fe(salen)Cl complex (32 mg, 0.10 mmol) and THF (10 mL), and the mixture was cooled to −30° C. A solution of phenylmagnesium bromide (1M in THF, 4.8 mL, 4.8 mmol) is added via syringe to the resulting red solution, causing an immediate color change to dark brown/black. The resulting mixture is stirred for 10 min at this temperature, is then diluted with Et$_2$O and carefully quenched with saturated NaCl. Standard extractive work-up followed by flash chromatography (hexanes:EtOAc 10:1) provides the cross-coupling product as a white solid (386 mg, 66%). mp=118–120° C. $^1$H NMR (400 MHz, CDCl$_3$) δ 8.72 (m, 2H), 8.16 (d, J=8.3 Hz, 1H), 8.13 (dt, J=8.3, 0.4 Hz, 1H), 7.89 (m, 3H), 7.64–7.49 (m, 7H); $^{13}$C NMR (100 MHz, CDCl$_3$) (DEPT) δ 168.31 (C), 160.25 (C), 152.01 (C), 138.24 (C), 137.73 (C), 133.48 (CH), 130.47 (CH), 130.17 (CH), 129.88 (CH), 129.19 (CH), 128.68 (CH), 128.51 (2×CH), 126.99 (CH), 126.96 (CH), 121.70 (C). IR: υ (cm$^{-1}$, KBr) 3053, 1613, 1564, 1540, 1486, 1342, 774, 702. MS (EI): m/z (rel. intensity): 282 (80, [M$^+$]), 281 (100), 205 (7), 178 (8), 141 (6), 102 (4), 77 (8). HR-MS calcd. for C$_{20}$H$_{14}$N$_2$ 282.1157; found 282.1157.

EXAMPLE 17

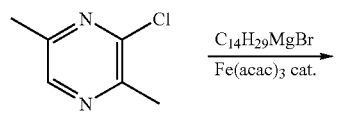

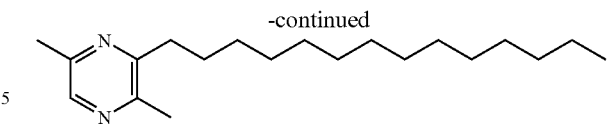

A flame-dried two necked round bottom flask is charged under Ar with 6-chloro-2,5-dimethylpyrazine (500 mg, 3.51 mmol), Fe(acac)$_3$ (60 mg, 0.17 mmol), THF (15 mL) and NMP (2.2 mL, 22.8 mmol). A solution of n-tetradecylmagnesium bromide (1M in THF, 4.6 mL, 4.6 mmol) is added via syringe to the resulting red solution causing an immediate color change to dark brown. The resulting mixture is stirred for 5–10 min, diluted with Et$_2$O and carefully quenched with brine. Standard extractive work-up followed by column chromatography (hexanes:EtOAc 10:1) provides the cross-coupling product as a white solid (1010 mg, 94%). mp=35–36° C. $^1$H NMR (400 MHz, CDCl$_3$) δ 8.14 (s, 1H), 2.76 (t, J=8.0 Hz, 2H), 2.52 (s, 3H), 2.48 (s, 3H), 1.65 (m, 2H), 1.41–1.28 (m, 22H), 0.87 (m, 3H); $^{13}$C NMR (100 MHz, CDCl$_3$) (DEPT) δ 154.99 (C), 150.04 (C), 148.45 (C), 140.52 (CH), 35.16 (CH$_2$), 31.92 (CH$_2$), 29.08 (CH$_2$), 29.65 (CH$_2$), 29.63 (CH$_2$), 29.55 (CH$_2$), 29.48 (CH$_2$), 29.35 (CH$_2$), 28.67 (CH$_2$), 22.68 (CH$_2$), 21.10 (CH$_3$), 21.02 (CH$_3$), 14.09 (CH$_3$); IR: υ (cm$^{-1}$) 2954, 2914, 2850, 1473, 1453, 1377, 1370; MS (EI): m/z (rel. intensity): 304 (5, [M$^+$]), 289 (3), 135 (9), 122 (100). Anal. Calcd. for C$_{20}$H$_{36}$N$_2$: C, 78.88; H, 11.92. Found: C, 78.77; H, 11.86.

EXAMPLE 18

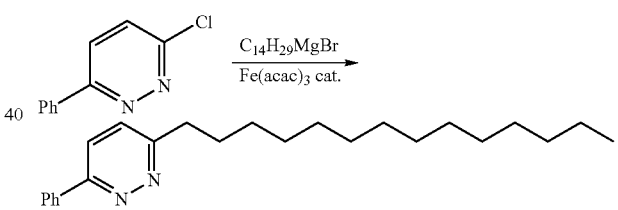

A flame-dried two necked round bottom flask is charged under Ar with 6-chloro-3-phenylpyridazine (500 mg, 2.62 mmol), Fe(acac)$_3$ (46 mg, 0.13 mmol), THF (15 mL) and NMP (1.3 mL, 17.0 mmol). A solution of n-tetradecylmagnesium bromide (1M in THF, 3.4 mL, 3.4 mmol) is added via syringe to the resulting red solution causing an immediate color change to dark brown. The resulting mixture is stirred for 5–10 min, diluted with Et$_2$O and carefully quenched with brine. Standard extractive work-up followed by column chromatography (hexanes:EtOAc 10:1, then 5:1) provides the cross-coupling product as a white solid (634 mg, 68%). mp=87–88° C. $^1$H NMR (400 MHz, CDCl$_3$) δ 8.09–8.03 (m, 2H), 7.77 (d, J=8.7 Hz, 1H), 7.45–7.47 (m, 3H), 7.37 (d, J=8.7 Hz, 1H), 3.02 (t, J=6.7 Hz, 2H), 1.81 (m, 2H), 1.44–1.20 (m, 22H), 0.88 (m, 3H); $^{13}$C NMR (100 MHz, CDCl$_3$) (DEPT) δ 162.31 (C), 157.32 (C), 136.34 (C), 129.82 (CH), 128.96 (CH), 126.72 (CH), 124.16 (CH), 35.79 (CH$_2$), 31.91 (CH$_2$), 29.65 (CH$_2$), 29.63 (CH$_2$), 29.53 (CH$_2$), 29.51 (CH$_2$), 29.44 (CH$_2$), 29.34 (CH$_2$), 29.26 (CH$_2$), 22.67 (CH$_2$), 14.09 (CH$_3$); IR: υ (cm$^{-1}$) 3060, 2916, 2848, 1590, 1469, 1450, 747, 693; MS (EI): m/z (rel. intensity): 352 (11, [M$^+$]), 183 (20), 170 (100), 141 (2), 102

(3). Anal. Calcd. for $C_{24}H_{36}N_2$: C, 81.76; H, 10.29. Found: C, 81.65; H, 10.21. HRMS Calcd. for $C_{24}H_{36}N_2$: 352.2879. Found: 352.2879.

EXAMPLE 19

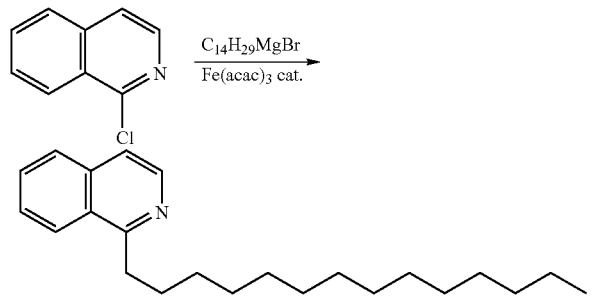

A flame-dried two necked round bottom flask is charged under Ar with 1-chloroisoquinoline (500 mg, 3.06 mmol), Fe(acac)$_3$ (58 mg, 0.16 mmol), THF (15 mL) and NMP (1.9 mL, 19.8 mmol). A solution of n-tetradecylmagnesium bromide (1M in THF, 4.0 mL, 4.0 mmol) is added via syringe to the resulting red solution causing an immediate color change to dark brown. The resulting mixture is stirred for 5–10 min, diluted with Et$_2$O and carefully quenched with brine. Standard extractive work-up followed by column chromatography (hexanes:EtOAc 10:1) provides the cross-coupling product as a white solid (946 mg, 95%). mp=34–36° C. $^1$H NMR (400 MHz, CDCl$_3$) δ 8.43 (d, J=6.0 Hz, 1H), 8.15 (d, J=8.2 Hz, 1H), 7.80 (d, J=8.2 Hz, 1H), 7.66 (bt, J=7.2 Hz, 1H), 7.58 (bt, J=7.2 Hz, 1H), 7.49 (d, J=6.0 Hz, 1H) (m, 2H), 3.30 (t, J=7.9 Hz, 2H), 1.86 (m, 2H), 1.49–1.22 (m, 22H), 0.87 (m, 3H); $^{13}$C NMR (100 MHz, CDCl$_3$) (DEPT) δ 162.45 (C), 141.71 (CH), 136.31 (C), 129.79 (CH), 127.37 (CH), 126.93 (CH), 125.39 (CH), 119.13 (CH), 35.49 (CH$_2$), 31.91 (CH$_2$), 29.91 (CH$_2$), 29.82 (CH$_2$), 29.66 (CH$_2$), 29.63 (CH$_2$), 29.57 (CH$_2$), 29.53 (CH$_2$), 29.34 (CH$_2$), 22.67 (CH$_2$), 14.08 (CH$_3$); IR: υ (cm$^{-1}$) 3051 br, 3049, 2916, 2848, 1563, 1502, 1468, 1386, 824, 749; MS (EI): m/z (rel. intensity): 325 (8, [M$^+$]), 198 (3), 156 (17), 143 (100), 115 (3), 43 (4). Anal. Calcd. for $C_{23}H_{35}N$: C, 84.86; H, 10.84. Found: C, 84.82; H, 10.97.

EXAMPLE 20

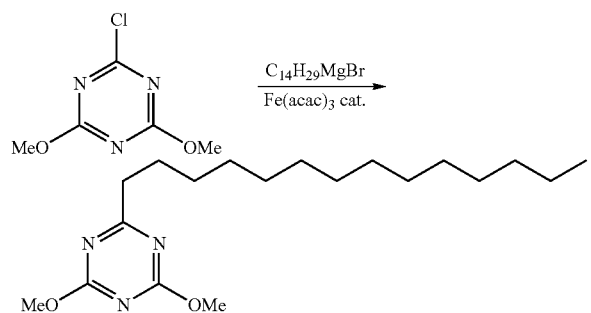

A flame-dried two necked round bottom flask is charged under Ar with 2-chloro-4,6-dimethoxytriazine (500 mg, 2.85 mmol), Fe(acac)$_3$ (50 mg, 0.14 mmol), THF (10 mL) and NMP (1.8 mL, 18.5 mmol). A solution of n-tetradecylmagnesium bromide (1M in THF, 3.7 mL, 3.7 mmol) is added via syringe to the resulting red solution causing an immediate color change to dark brown. The resulting mixture is stirred for 5–10 min, diluted with Et$_2$O and carefully quenched with brine. Standard extractive work-up followed by column chromatography (hexanes:EtOAc 5:1) provides the cross-coupling product as a white solid (754 mg, 84%). mp=51–52° C. $^1$H NMR (400 MHz, CDCl$_3$) δ 3.96 (bs, 6H), 2.65 (t, J=7.6 Hz, 2H), 1.71 (m, 2H), 1.39–1.12 (m, 22H), 0.88 (m, 3H); $^{13}$C NMR (100 MHz, CDCl$_3$) (DEPT) δ 183.53 (C), 172.36 (C), 54.82 (CH$_3$), 38.56 (CH$_2$), 31.80 (CH$_2$), 29.55 (CH$_2$), 29.51 (CH$_2$), 29.37 (CH$_2$), 29.23 (CH$_2$), 29.17 (CH$_2$), 27.23 (CH$_2$), 22.55 (CH$_2$), 13.94 (CH$_3$); IR: υ (cm$^{-1}$) 3003, 2955, 2915, 2851, 1588, 1553, 1502, 1472, 1355, 1072, 817, 716; MS (EI): m/z (rel. intensity): 377 (4, [M$^+$]), 322 (2), 168 (31), 155 (100), 125 (2), 43 (11). Anal. Calcd. for $C_{19}H_{35}N_3O_2$: C, 67.62; H, 10.45. Found: C, 67.54; H, 10.40.

EXAMPLE 21

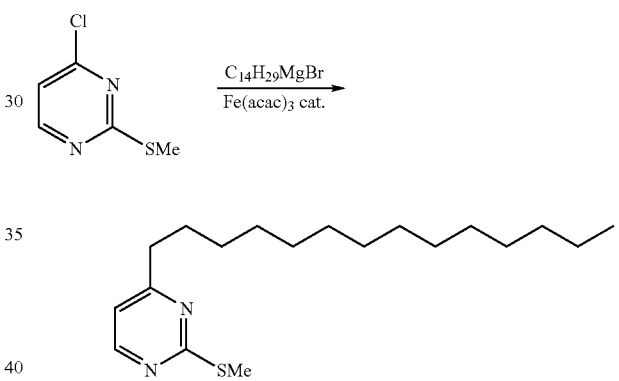

A flame-dried two necked round bottom flask is charged under Ar with 4-chloro-2-(methylthio)pyrimidine (500 mg, 3.11 mmol), Fe(acac)$_3$ (55 mg, 0.16 mmol), THF (10 mL) and NMP (2 mL). A solution of n-tetradecylmagnesium bromide (1M in THF, 3.7 mL, 3.7 mmol) is added via syringe to the resulting red solution causing an immediate color change to dark brown. The resulting mixture is stirred for 5–10 min, diluted with Et$_2$O and carefully quenched with saturated NaCl. Standard extractive work-up followed by column chromatography (hexanes:EtOAc 5:1) provides the cross-coupling product as a colorless syrup (896 mg, 89%). $^1$H NMR (400 MHz, CDCl$_3$) δ 8.37 (d, J=5.1 Hz, 1H), 6.80 (d, J=5.1 Hz, 1H), 2.67 (t, J=7.6 Hz, 2H), 2.56 (bs, 3H), 1.72 (m, 2H), 1.32–1.22 (m, 22H), 0.88 (m, 3H); $^{13}$C NMR (100 MHz, CDCl$_3$) (DEPT) δ 172.20 (C), 171.37 (C), 156.63 (CH), 115.31 (CH), 37.78 (CH$_2$), 31.96 (CH$_2$), 29.72 (CH$_2$), 29.54 (CH$_2$), 29.42 (CH$_2$), 29.39 (CH$_2$), 29.31 (CH$_2$), 28.61 (CH$_2$), 22.72 (CH$_2$), 14.13 (CH$_3$), 14.07 (CH$_3$); IR: υ (cm$^{-1}$) 3032, 2924, 2853, 1568, 1542, 1466, 1423, 1335, 1205; MS (EI): m/z (rel. intensity): 322 (7, [M$^+$]), 209 (2), 153 (16), 140 (100), 94 (3), 43 (4). Anal. Calcd. for $C_{19}H_{34}N_2S$: C, 70.75; H, 10.62. Found: C, 70.65; H, 10.54. HRMS Calcd. for $C_{19}H^{34}N_2S$: 322.2443. Found: 322.2442.

EXAMPLE 22

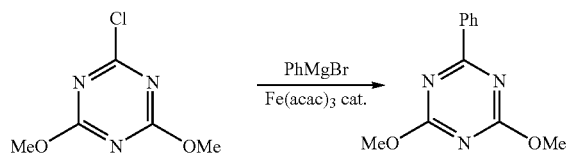

A solution of phenylmagnesium bromide (1M in THF, 3.9 mL, 3.9 mmol) is added to a solution of 2-chloro-4,6-dimethoxy-1,3,5-triazine (300 mg, 1.70 mmol) and Fe(acac)$_3$ (30 mg, 0.085 mmol) in THF (10 mL) at −30° C. After stirring for 30 min at that temperature, the reaction is quenched with brine, the aqueous layer is extracted with Et$_2$O, the combined organic phases are dried over Na$_2$SO$_4$ and evaporated, and the residue is purified by flash chromatography (hexane/ethyl acetate, 10:1). After eluting a first fraction containing biphenyl (103 mg), one obtains 2-phenyl-4,6-dimethoxy-1,3,5-triazine as a colorless solid (231 mg, 63%). $^1$H NMR (300 MHz, CD$_2$Cl$_2$) δ 8.47 (d, 2H), 7.47–7.56 (m, 3H), 4.08 (s, 3H). $^{13}$C NMR (75 MHz, CD$_2$Cl$_2$) δ 175.0, 173.3, 135.6, 133.0, 129.2, 128.8, 55.4.

EXAMPLE 23

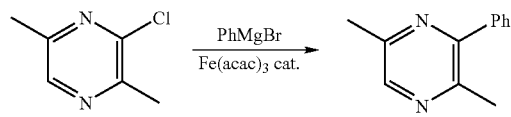

A solution of phenylmagnesium bromide (1M in THF, 5.6 mL, 5.6 mmol) is added to a solution of 3-chloro-2,5-dimethylpyrazine (346 mg, 2.42 mmol) and Fe(acac)$_3$ (43 mg, 0.12 mmol) in THF (10 mL) at −30° C. After stirring for 30 min at that temperature, the reaction is quenched with brine, the aqueous layer is extracted with Et$_2$O, the combined organic phases are dried over Na$_2$SO$_4$ and evaporated, and the residue is purified by flash chromatography (hexane/ethyl acetate, 10:1). After eluting a first fraction containing biphenyl (212 mg), one obtains 2,5-dimethyl-3-phenylpyrazine as a pale yellow syrup (287 mg, 64%). $^1$H NMR (300 MHz, CD$_2$Cl$_2$) δ 8.31 (s, 1H), 7.55–7.59 (m, 2H), 7.43–7.51 (m, 3H), 2.55 (s, 3H), 2.54 (s, 3H). $^{13}$C NMR (75 MHz, CD$_2$Cl$_2$) δ 152.7, 150.6, 148.4, 142.1, 139.5, 129.3, 128.7, 128.6, 22.7, 21.2.

EXAMPLE 24

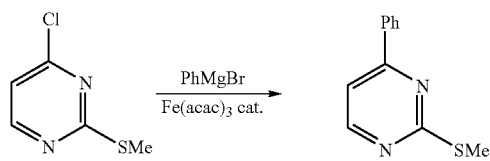

A solution of phenylmagnesium bromide (1M in THF, 4.2 mL, 4.2 mmol) is added to a solution of 4-chloro-2-methylthio-pyrimidine (296 mg, 1.84 mmol) and Fe(acac)$_3$ (32 mg, 0.09 mmol) in THF (10 mL) at −30° C. After stirring for 50 min at that temperature, the reaction is quenched with brine, the aqueous layer is extracted with Et$_2$O, the combined organic phases are dried over Na$_2$SO$_4$ and evaporated, and the residue is purified by flash chromatography (hexane/ethyl acetate, 10:1). After eluting a first fraction containing biphenyl (90 mg), one obtains 2-methylthio-4-phenyl-pyrimidine as a pale yellow solid (197 mg, 53%). $^1$H NMR (300 MHz, CD$_2$Cl$_2$) δ 8.53 (d, 1H), 8.09–8.13 (m, 2H), 7.53–7.48 (m, 3H), 7.39 (d, 2H), 2.63 (s, 3H); $^{13}$C NMR (75 MHz, CD$_2$Cl$_2$) δ 173.0, 164.0, 158.0, 136.7, 131.1, 131.0, 129.2, 127.5, 127.4, 112.2, 14.3.

EXAMPLE 25

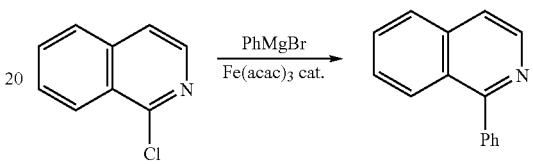

A solution of phenylmagnesium bromide (1M in THF, 3.6 mL, 3.6 mmol) is added to a solution of 2-chloro-isoquinoline (258 mg, 1.57 mmol)) and Fe(acac)$_3$ (28 mg, 0.078 mmol) in THF (10 mL) at −30° C. After stirring for 50 min at that temperature, the reaction is quenched with brine, the aqueous layer is extracted with Et$_2$O, the combined organic phases are dried over Na$_2$SO$_4$ and evaporated, and the residue is purified by flash chromatography (hexane/ethyl acetate, 10:1). After eluting a first fraction containing biphenyl (60 mg), one obtains 2-phenyl-isoquinoline as a colorless solid (184 mg, 57%). $^1$H NMR (300 MHz, CD$_2$Cl$_2$) δ 8.60 (d, 1H), 8.11 (d, 1H), 7.91 (d, 1H), 7.66–7.72 (m, 4H), 7.48–7.57 (m, 4H); $^{13}$C NMR (75 MHz, CD$_2$Cl$_2$) δ 160.9, 142.6, 140.1, 137.2, 130.3, 130.2, 128.8, 128.5, 127.7, 127.5, 127.3, 127.0, 120.1.

EXAMPLE 26

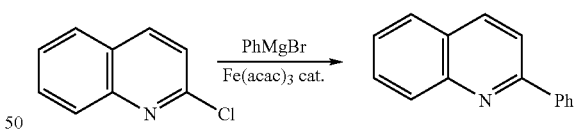

A solution of phenylmagnesium bromide (1M in THF, 4.2 mL, 4.2 mmol) is added to a solution of 2-chloro-quinoline (300 mg, 1.83 mmol)) and Fe(acac)$_3$ (32 mg, 0.09 mmol) in THF (10 mL) at −30° C. After stirring for 50 min at that temperature, the reaction is quenched with brine, the aqueous layer is extracted with Et$_2$O, the combined organic phases are dried over Na$_2$SO$_4$ and evaporated, and the residue is purified by flash chromatography (hexane/ethyl acetate, 15:1). After eluting a first fraction containing biphenyl (44 mg), one obtains 2-phenyl-quinoline as a colorless solid (265 mg, 71%). $^1$H NMR (300 MHz, CD$_2$Cl$_2$) δ 8.22–8.25 (m, 3H), 8.16 (d, 1H), 7.92 (d, 1H), 7.86 (d, 1H), 7.75 (m, 1H), 7.46–7.57 (m, 4H); $^{13}$C NMR (75 MHz, CD$_2$Cl$_2$) δ 157.3, 148.7, 139.9, 137.0, 130.0, 129.7, 129.1, 127.8, 127.7, 127.6, 127.3, 126.8, 119.1.

EXAMPLE 27

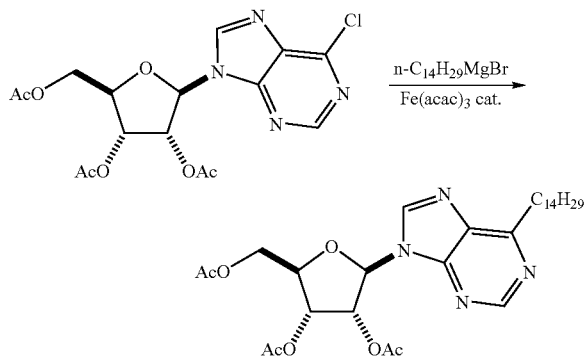

To a solution of Fe(acac)$_3$ (14 mg, 0.04 mmol) and NMP (0.34 mL, 3.5 mmol) in THF (2 mL) under Ar at room temperature is added n-tetradecylmagnesium bromide (1M in THF, 0.3 mL, 0.3 mmol) causing the reaction color to change from red to dark brown. A solution of 2',3',5'-tri-O-acetyl-6-chloro-9-β-D-ribofuranosyl-purine (220 mg, 0.53 mmol) in THF (5 mL) is then added via cannula, followed by addition of a second dose of n-tetradecylmagnesium bromide (1M in THF, 1.0 mL, 1.0 mmol). The resulting mixture is stirred for 10 min at that temperature prior to careful quenching with sat. NaCl and extraction with CH$_2$Cl$_2$. Flash chromatography (hexanes:EtOAc, 1:1) provides the cross-coupling product as a yellow oil (170 mg, 56%). $^1$H NMR (400 MHz, CDCl$_3$) δ 8.87 (s, 1H), 8.15 (s, 1H), 6.21 (d, J=5.2 Hz, 1H), 5.97 (t, J=5.4 Hz, 1H), 5.69 (t, J=5.1 Hz, 1H), 4.44 (m, 2H), 4.36 (dd, J=18.2, 5.3 Hz, 1H), 3.18 (t, J=7.7 Hz, 2H), 2.14 (s, 3H), 2.10 (s, 3H), 2.07 (s, 3H), 1.87 (m, 2H), 1.41 (m, 2H), 1.38–1.22 (m, 22H), 0.86 (t, J=6.5 Hz, 3H); $^{13}$C NMR (100 MHz, CDCl$_3$) (DEPT) δ 170.24 (C), 169.50 (C), 163.79 (C), 152.68 (CH), 150.24 (C), 141.91 (CH), 133.26 (C), 86.45 (CH), 80.31 (CH), 73.07 (CH), 70.59 (CH), 62.99 (CH$_2$), 33.34 (CH$_2$), 31.87 (CH$_2$), 29.64 (CH$_2$), 29.60 (CH$_2$), 29.48 (CH$_2$), 29.40 (CH$_2$), 29.30 (CH$_2$), 28.52 (CH$_2$), 22.64 (CH$_2$), 20.68 (CH$_3$), 20.47 (CH$_3$), 20.34 (CH$_3$), 14.06 (CH$_3$).

We claim:

1. A process for producing a compound of the formula Ar—(R$^1$)$_p$(X)$_{n-p}$, said process comprising conducting a cross-coupling reaction between at least one organometallic reagent of the formula (R$^1$)-M and an aromatic or heteroaromatic substrate of the formula Ar—(X)$_n$ in a reaction mixture in the presence of at least one catalyst or precatalyst comprising one or several iron salts or iron complexes containing iron in an oxidation state of −2, −1, 0, +1, +2 or +3, said iron complexes not comprising palladium, and said iron salts or iron complexes being present in the reaction mixture homogeneously or heterogeneously, wherein in said formulas:
Ar represents an optionally annellated C$_6$–C$_{30}$ aromatic or heteroaromatic group;
each X independently represents halide, suiphonate or phosphonate;
each R$^1$ independently represents C$_1$–C$_{20}$ linear or branched alkyl, C$_3$–C$_{20}$ cycloalkyl, C$_6$–C$_{20}$ aryl or heteroaryl; said alkyl or aryl groups optionally being substituted by any substituent that is inert under the conditions of said reaction to (R$^1$)-M;++
M represents MgZ, CaZ, ZnZ, MnZ or (ZnR$^{60}$R$^{61}$)MgZ;
R$^{60}$ and R$^{61}$ independently represent C$_1$–C$_{20}$ linear or branched alkyl, C$_3$–C$_{10}$ cycloalkyl, C$_6$–C$_{20}$ aryl or heteroaryl, which may be unsubstituted or substituted by any substituent which is inert under the conditions of said reaction to (ZnR$^{60}$R$^{61}$)MgZ;
Z represents any anionic ligand; and
n and peach represent at least 1 provided that if n=1, then p=1, and if n>1, then p=1 or n.

2. A process for producing a compound of the formula Ar—(R$^1$)$_p$(X)$_{n-p}$, said process comprising conducting a cross-coupling reaction between at least one organometallic reagent of the formula (R$^1$)-M and an aromatic or heteroaromatic substrate of the formula Ar—(X)$_n$ in a reaction mixture in the presence of at least one catalyst or precatalyst comprising one or several iron salts or iron complexes containing iron in an oxidation state of −2, −1, 0, +1, +2 or +3, said iron complexes not comprising palladium, and said iron salts or iron complexes being present in the reaction mixture homogeneously or heterogeneously, wherein in said formulas:
Ar represents an optionally annellated C$_6$–C$_{30}$ aromatic or heteroaromatic group;
each X independently represents halide, suiphonate or phosphonate;
each R$^1$ independently represents C$_1$–C$_{20}$ linear or branched alkyl, C$_3$–C$_{20}$ cycloalkyl, C$_6$–C$_{20}$ aryl or heteroaryl; said alkyl or aryl groups optionally being substituted by any substituent that is inert under the conditions of said reaction to (R$^1$)-M;
M represents MgZ, CaZ, ZnZ, MnZ or (ZnR$^{60}$R$^{61}$)MgZ;
R$^{60}$ and R$^{61}$ independently represent C$_1$–C$_{20}$ linear or branched alkyl, C$_3$–C$_{10}$ cycloalkyl, C$_6$–C$_{20}$ aryl or heteroaryl, which may be unsubstituted or substituted by any substituent which is inert under the conditions of said reaction to (ZnR$^{60}$R$^{61}$)MgZ;
Z represents any anionic ligand; and,
n and p each represent 1 or 2 provided that if n=1, then p=1, and if n=2, then p=1 or 2.

3. The process according to claim 1, wherein said iron salts or iron complexes are independently selected from the group consisting of finely dispersed metallic iron, FeF$_2$, FeF$_{2.4}$ H$_2$O, FeF$_3$, FeF$_{3.3}$ H$_2$O, FeCl$_2$, FeCl$_{2.4}$ H$_2$O, FeCl$_3$, FeCl$_{3.6}$ H$_2$O, FeCl$_3$(PPh$_3$), Fe(OEt)$_2$, Fe(OEt)$_3$, FeCl$_2$.(PPh$_3$)$_2$, FeCl$_2$.(ddpe) [ddpe=1,2-bis-(diphenylphosphino)-ethane], Fe(acac)$_2$ [acac=acetylacetonate], Fe(acac)$_3$, tris-(trifluoroacetylacetonato)iron (III), tris-(hexafluoroacetylacetonato)iron (III), tris-(dibenzoylmethido)iron (III), tris-(2,2,6,6-tetramethyl-3,5-diheptanedionato)iron (III), FeBr$_2$, FeBr$_3$, FeI$_2$, Fe(II) acetate, Fe(II)oxalate, Fe(II)stearate, Fe(II)citrate.Hydrate, Fe(II)pivalate, Fe(II)-D-gluconate.2 H$_2$O, Fe(OSO$_2$C$_6$H$_4$Me)$_3$, Fe(OSO$_2$C$_6$H$_4$Me)$_3$.Hydrate, FePO$_4$, Fe(NO$_3$)$_3$, Fe(NO$_3$)$_{3.9}$ H$_2$O Fe(ClO$_4$)$_2$.Hydrat FeSO$_4$, FeSO$_4$.Hydrate, Fe$_2$(SO$_4$)$_3$, Fe$_2$(SO$_4$)$_3$.Hydrate, K$_3$Fe(CN)$_6$, ferrocene, bis(pentamethylcyclopentadienyl)iron, bis(indenyl)iron, Fe(II)phthalocyanin, Fe(III)phthalocyanin chloride, Fe(III)-2,2,6,6-tetramethyl-3,5-heptanedioate, Fe(CO)$_5$, Fe(salen)X [salen=N,N-ethylenebis(salicylidenamidato), X=Cl, Br, I], 5,10,15,20-tetraphenyl- 21H,23H-porphin-iron (III) halide, 5,10,15,20-tetrakis(pentafluorophenlyl)-21H, 23H-porphin-iron(III) halide, and iron-magnesium intermetallic compounds.

4. The process according to claim 1, wherein said group Ar is phenyl, unsubstituted or substituted with 1–5 identical or different substituents selected from the group consisting of C$_1$–C$_{10}$ linear or branched alkyl, C$_3$–C$_{10}$ cycloalkyl, C$_1$–C$_{10}$ linear or branched perfluoroalkyl, C$_2$–C$_{10}$ alkenyl, $C_2$–$C_{10}$ alkynyl, $C_6$–$C_{20}$ aryl or heteroaryl, —COOR$^2$, —OR$^3$, —CN, —SR$^4$, —SOR$^5$, —SO$_2$R$^6$, —SO$_2$(OR$^7$), —SO$_2$(NR$^8$R$^9$), —COR$_{10}$, —NR$^{11}$R$^{12}$, —CONR$^{13}$R$^{14}$, —F, —Cl, —SiR$^{15}$R$^{16}$R$^{17}$, —PR$^{18}$R$^{19}$, —P(O)R$^{20}$R$^{21}$, —P(O)(OR$^{22}$)(OR$^{23}$), —P(O)(NR$^{24}$R$^{25}$)(NR$^{26}$R$^{27}$), —NCO, —NCS, —OC(O)OR$^{28}$, —OC(S)OR$^{29}$, —OC(O)NR$^{30}$R$^{31}$, —NR$^{32}$C(O)OR$^{33}$, —NR$^{34}$C(O)NR$^{35}$R$^{36}$, —C(OR$^{37}$)$_2$, —C(OR$^{38}$)(OR$^{39}$), —OC(O)R$^{40}$, —NR$^{41}$C(O)R$^{42}$, —SC(O)R$^{43}$, —N=R$^{44}$, —OSO$_2$R$^{45}$, —NR$^{46}$SO$_2$R$^{47}$, —C(NR$^{48}$)(OR$^{49}$), —N=NR$^{50}$R$^{51}$, —NO$_2$, C(OR$^{52}$)$_3$, —C(SR$^{53}$)$_2$, —OSiR$^{54}$R$^{55}$R$^{56}$, with R$^2$–R$^{56}$ are independently chosen from: H, $C_1$–$C_{10}$ linear or branched alkyl, $C_3$–$C_{10}$ cycloalkyl, $C_1$–$C_{10}$ linear or branched perfluoroalkyl, $C_2$–$C_{10}$ alkenyl, $C_2$–$C_{10}$ alkynyl, $C_6$–$C_{20}$ aryl or heteroaryl; said phenyl ring optionally being annellated to one or more other rings of any ring size, said rings being aromatic, heteroaromatic or non-aromatic.

5. The process according to claim 1, wherein said group Ar is a heteroaromatic five-membered ring or six-membered ring with 1–4 heteroatoms for the five-membered ring or 1–5 heteroatoms for the six-membered ring, respectively, which may be identical or not identical and selected from the group consisting of N, S, O and P; said heteroaromatic five-membered ring or six-membered ring optionally being annellated to one or more other rings of any ring size, said other rings being aromatic, heteroaromatic, or non-aromatic, and optionally being substituted with 1–5 identical or different substituents selected from the group consisting of $C_1$–$C_{10}$ linear or branched alkyl, $C_3$–$C_{10}$ cycloalkyl, $C_1$–$C_{10}$ linear or branched perfluoroalkyl, $C_2$–$C_{10}$ alkenyl, $C_2$–$C_{10}$ alkynyl, $C_6$–$C_{20}$ arly or heteroaryl, —COOR$^2$, —OR$^3$, —CN, —SR$^4$, —SOR$^5$, —SO$_2$R$^6$, —SO$_2$(OR$^7$), —SO$_2$(NR$^8$R$^9$), —COR$^{10}$, NR$^{11}$R12, —CONR$^{13}$R$^{14}$, —F, —Cl, —SiR$^{15}$R$^{16}$R$^{17}$, —PR$^{18}$R$^{19}$, —P(O)R$^{20}$, R$^{21}$, —P(O)(OR$^{22}$)(OR$^{23}$), —P(O)(NR$^{24}$R$^{25}$)(NR$^{26}$R$^{27}$), —NCO, —NCS, —OC(O)OR$^{28}$, —OC(S)OR$^{29}$, —OC(O)NR$^{30}$R$^{31}$, —NR$^{32}$C(O)OR$^{33}$, —NR$^{34}$C(O)NR$^{35}$R$^{36}$, —C(OR$^{37}$)$_2$, —C(OR$^{38}$)(OR$^{39}$), —OC(O)R$^{40}$, —NR$^{41}$C(O)R$^{42}$, —SC(O)R$^{43}$, —N=R$^{44}$, —OSO$_2$R$^{45}$, —NR$^{46}$SO$_2$R$^{47}$, —C(NR(OR$^{49}$), —N=NR$^{50}$R$^{51}$, —NO$_2$, —C(OR$^{52}$)$_3$, —C(SR$^{53}$)$_2$, —OSiR$^{54}$R$^{55}$R$^{56}$, with R$^2$–R$^{56}$ being independently selected from the group consisting of H, $C_1$–$C_{10}$ linear or branched alkyl, $C_3$–$C_{10}$ cycloalkyl, $C_1$–$C_{10}$ linear or branched perfluoroalkyl, $C_2$–$C_{10}$ alkenyl, $C_2$–$C_{10}$ alkynyl, $C_6$–$C_{20}$ aryl and heteroaryl.

6. The process according to claim 1, in which said group X is chloride.

7. The process according to claim 1, in which said group X is —OSO$_2$R$^{57}$ or —OP(O)(OR$^{58}$)(OR$^{59}$) with R$^{57}$–R$^{59}$ being independently selected from the group consisting of $C_1$–$C_{10}$ linear or branched alkyl, $C_1$–$C_{10}$ cycloalkyl, $C_1$–$C_{10}$ perfluoroalkyl, $C_6$–$C_{20}$ aryl and heteroaryl; said alkyl, cycloalkyl, aryl or heteroaryl groups optionally being substituted with 1–5 identical or different substituents selected from the group consisting of $C_1$–$C_6$ branched or linear alkyl, $C_1$–$C_6$ perfluoroalkyl, $C_6$–$C_{20}$ aryl, —F and —CN.

8. The process according to claim 7, in which said group X is methanesulfonate, benzenesulfonate, toluenesulfonate, dimethylbenzenesulfonate, trimethylbenzenesulfonate, triisopropylbenzcnesulfonate, fluorobenzenesulfonate, difluorobenzenesulfoante, trifluorobenzenesulfonate, hexafluorobenzenesulfonate, methoxybenzenesulfonate, trifluoromethanesulfonate, or nonafluorobutanesulfonate (nonaflate).

9. The process according to claim 1, in which said organometallic reagent (R$^1$)-M is a Grignard reagent, wherein
each R$^1$ independently represents $C_1$–$C_{20}$ linear or branched alkyl, $C_3$–$C_{20}$ cycloalkyl, $C_6$–$C_{20}$ aryl or heteroaryl; said alkyl or aryl groups optionally being substituted by any substituent which is inert under the reaction conditions towards magnesium;
M represents MgZ, wherein
Z represents fluoride, chloride, bromide or iodide.

10. The process according to claim 1, in which said organometallic reagent (R$^1$)-M is a diorganomagnesium reagent, wherein
each R$^1$ independently represents any $C_1$–$C_{20}$ linear or branched alkyl, $C_3$–$C_{20}$ cycloalkyl, $C_6$–$C_{20}$ aryl or heteroaryl; said alkyl or aryl groups may be substituted by any substituent which is inert under the reaction conditions towards magnesium;
M represents MgZ, wherein
Z represents any $C_1$–$C_{20}$ linear or branched alkyl, $C_3$–$C_{20}$ cycloalkyl, $C_6$–$C_{20}$ aryl or heteroaryl.

11. The process according to claim 1, in which said organometallic reagent (R$^1$)-M is a triorganozincate, wherein
M represents (ZnR$^{60}$R$^{61}$)MgZ wherein R$^{60}$ and R$^{61}$ independently represent any $C_1$–$C_{20}$ linear or branched alkyl, $C_3$–$C_{10}$ cycloalkyl, $C_6$–$C_{20}$ aryl or heteroaryl, which may be substituted or unsubstituted by any substituent which is inert under the reaction conditions towards (ZnR$^{60}$R$^{61}$)MgZ, wherein
Z represents fluoride, chloride, bromide or iodide.

12. The process according to claim 1, in which said aromatic or heteroaromatic substrates contain more than one X group which may be identical or not identical.

13. A process according to claim 12, in which only one of said X groups is selectively replaced during the cross coupling reaction by an organic residue R$^1$ while the others of said X groups are preserved in the cross coupling product formed.

14. The process according to claim 12, in which all of said X groups, which may be identical or not identical, are replaced during the cross coupling process by organic residues R$^1$, which may be identical or different.

15. The process according to claim 12, in which said groups X are consecutively replaced during the process by organic residues R$^1$ that are non-identical by consecutive addition of organometallic reagents R$^1$-M having different R$^1$ residues to the reaction mixture containing said substrate and one or several iron catalysts or iron precatalysts.

16. The process according to claim 1, in which said cross coupling reaction is performed in a reaction medium containing one or more ethereal solvents or hydrocarbon solvents.

17. The process according to claim 16, in which said ethereal solvents or hydrocarbon solvents are selected from the group consisting of diethyl ether, tetrahydrofuran, tetrahydropyran, methyl-tetrahydrofuran, 1,4-dioxane, tert-butyl methyl ether, dibutyl ether, di-isopropyl ether, dimethoxyethane, dimethoxymethane, pentane, hexane, heptane, octane, isooctane, cyclohexane, benzene, toluene, xylene, cymene, petrol ether and decaline.

18. The process according to claim 1, in which said cross coupling reaction is performed in a reaction medium containing one or more aprotic dipolar solvents.

19. The process according to claim 18, in which said aprotic dipolar solvent is selected from the group consisting of dimethylformamide, dimethylacetamide, dimethylsulfoxide, N-methylpyrrolidinone (NMP), tetramethylurea, sulfolane, diethyl carbonate, 1,3-dimethyltetrahydro-2(1H)-pyrimidinone (DMPU), hexamethyiphosphoric acid triamide (HMPA) and N,N,N',N'-tetramethylethylenediamine (TMEDA).

20. The process according to claim 1, in which said cross coupling reaction is performed in a reaction medium containing one or more ethereal or hydrocarbon solvents selected from the group consisting of diethyl ether, tetrahydrofuran, tetrahydropyran, methyl-tetrahydrofuran, 1,4-dioxane, tert-butyl methyl ether, dibutyl ether, di-isopropyl ether, dimethoxyethane, dimethoxymethane, pentane, hexane, heptane, octane, isooctane, cyclohexane, benzene, toluene, xylene, cymene, petrol ether and decaline, as well as one or more aprotic dipoiar solvents selected from the group consisting of dimethylformamide, dimethylacetamide, dimethylsulfoxide, N-methylpyrrolidinone (NMP), tetramethylurea, sulfolane, diethyl carbonate, 1,3-dimethyltetrahydro-2(1H)-pyrimidinone (DMPU), hexamethyiphosphoric acid triarmde (HMPA) and N,N,N',N'-tetramethylethylenediamine (TMEDA).

* * * * *

UNITED STATES PATENT AND TRADEMARK OFFICE
CERTIFICATE OF CORRECTION

PATENT NO. : 7,026,478 B2  
APPLICATION NO. : 10/143404  
DATED : April 11, 2006  
INVENTOR(S) : Fürstner et al.

Page 1 of 1

It is certified that error appears in the above-identified patent and that said Letters Patent is hereby corrected as shown below:

In the Specification

Column 3, line 37, "$R^{56 \text{ with } R2} - R^{56}$" should read -- $R^{56}$ with $R^2 - R^{56}$ --

Column 23, line 14, "10.38." should read -- 10.38; --

Column 23, line 54, "10.50." should read -- 10.50; --

Column 24, line 35, "10.78." should read -- 10.78; --

Column 26, line 30, "11.92." should read -- 11.92; --

Column 27, line 46, "10.84." should read -- 10.84; --

Column 28, line 21, "10.45." should read -- 10.45; --

Column 28, line 66, "10.62." should read -- 10.62; --

In the Claims

Column 33, line 3, "$-COR_{10}$" should read -- $-COR^{10}$ --

Column 33, line 10, "$-^{-NO}2$" should read -- $-NO_2$, --

Column 33, line 41, "$-C(NR$" should read -- $-C(NR^{48})$ --

Signed and Sealed this  
Twenty-fourth Day of December, 2013

Margaret A. Focarino  
*Commissioner for Patents of the United States Patent and Trademark Office*